(12) United States Patent
Miyoshi et al.

(10) Patent No.: US 9,393,001 B2
(45) Date of Patent: Jul. 19, 2016

(54) OPERATION METHOD OF ENDOSCOPE

(75) Inventors: Shunichiro Miyoshi, Tokyo (JP); Takehiro Kimura, Tokyo (JP); Yoshiro Okazaki, Tokyo (JP); Masayuki Kobayashi, Tokyo (JP); Michihiro Sugahara, Tokyo (JP)

(73) Assignee: OLYMPUS CORPORATION, Tokyo (JP)

(\*) Notice: Subject to any disclaimer, the term of this patent is extended or adjusted under 35 U.S.C. 154(b) by 950 days.

(21) Appl. No.: 13/532,922

(22) Filed: Jun. 26, 2012

(65) Prior Publication Data

US 2013/0027531 A1 Jan. 31, 2013

Related U.S. Application Data

(60) Provisional application No. 61/512,969, filed on Jul. 29, 2011.

(51) Int. Cl.
| | | |
|---|---|---|
| *A62B 1/04* | (2006.01) | |
| *A61B 17/00* | (2006.01) | |
| *A61B 1/01* | (2006.01) | |
| *A61B 1/313* | (2006.01) | |
| *A61B 1/00* | (2006.01) | |

(52) U.S. Cl.
CPC ....... *A61B 17/00234* (2013.01); *A61B 1/00082* (2013.01); *A61B 1/01* (2013.01); *A61B 1/3132* (2013.01); *A61B 2017/00243* (2013.01)

(58) Field of Classification Search
CPC .............. A61B 17/00234; A61B 1/00082; A61B 1/3132; A61B 1/01; A61B 2017/00243
See application file for complete search history.

(56) References Cited

U.S. PATENT DOCUMENTS

| | | | |
|---|---|---|---|
| 6,221,006 B1* | 4/2001 | Dubrul | A61B 17/221 600/159 |
| 2004/0054363 A1* | 3/2004 | Vaska et al. | 606/27 |
| 2004/0064014 A1* | 4/2004 | Melvin et al. | 600/37 |
| 2004/0102804 A1* | 5/2004 | Chin | A61B 17/00008 606/190 |
| 2005/0154376 A1* | 7/2005 | Riviere et al. | 606/1 |
| 2005/0228452 A1* | 10/2005 | Mourlas et al. | 607/3 |
| 2009/0036900 A1* | 2/2009 | Moll | A61B 19/2203 606/130 |
| 2010/0240952 A1* | 9/2010 | Okazaki et al. | 600/109 |
| 2010/0331619 A1 | 12/2010 | Miyoshi et al. | |
| 2010/0331854 A1* | 12/2010 | Greenberg et al. | 606/129 |
| 2011/0301413 A1* | 12/2011 | Morimoto | 600/104 |
| 2012/0179013 A1* | 7/2012 | Saito | 600/339 |
| 2012/0303019 A1* | 11/2012 | Zhao et al. | 606/41 |

\* cited by examiner

*Primary Examiner* — Sath V Perungavoor
*Assistant Examiner* — Dakshesh Parikh
(74) *Attorney, Agent, or Firm* — Scully, Scott, Murphy & Presser, P.C.

(57) ABSTRACT

Disclosed is an operation method of an endoscope, the method comprising: a sheath insertion step of percutaneously inserting at least one sheath in a pericardial cavity of a heart; an insertion step of inserting a rigid scope in the sheath; a view field securing step for securing the view field for a surgical site within the pericardial cavity; a guide step for guiding the rigid scope to the surgical site; and an observation step of observing the surgical site with the rigid scope.

23 Claims, 23 Drawing Sheets

Schematic of common lesion sets employed in AF ablation

OPERATION METHOD OF ENDOSCOPE

CROSS-REFERENCE TO RELATED APPLICATIONS

This application claims the benefit of U.S. Provisional Application No. 61/512,969, filed Jul. 29, 2011.

BACKGROUND OF THE INVENTION

1. Field of the Invention

The present invention relates to an operation method of an endoscope, and particularly to an operation method which comprises inserting an endoscope in a percutaneous manner and guiding a distal end portion of the endoscope to the affected part of the heart.

2. Description of Related Art

So far, a technique to insert a flexible endoscope into a pericardial cavity, which is a space between the heart and the pericardium, has been employed for cases of insertion of an endoscope in a percutaneous manner (refer to Description of United States Patent Application, Publication No. 2010/0331619).

BRIEF SUMMARY OF THE INVENTION

The present invention provides an operation method of an endoscope, the method comprising: a sheath insertion step of percutaneously inserting at least one sheath in a pericardial cavity of a heart; an insertion step of inserting a rigid scope in the sheath; a view field securing step securing the view field for a surgical site within the pericardial cavity; a guide step for guiding the rigid scope to the surgical site; and an observation step of observing the surgical site with the rigid scope.

DETAILED DESCRIPTION OF THE INVENTION

Hereunder is a description of the operation method of an endoscope according to a first embodiment of the present invention with reference to the drawings.

Figure 1:
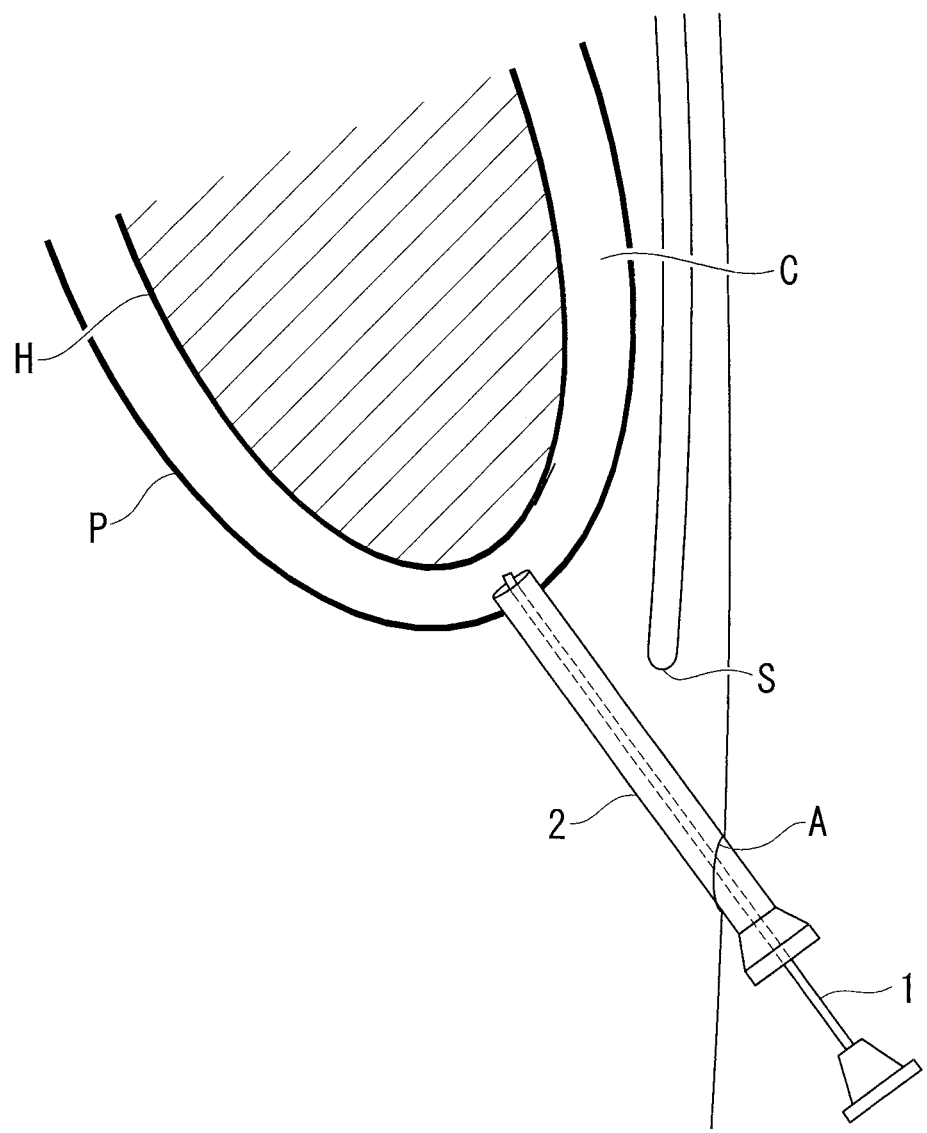
FIG. 1 is a cross-sectional view of the inside of a body showing that the endoscope is inserted in the pericardial cavity of the heart.

As shown in FIG. 1, in the operation method of an endoscope according to this embodiment, a rigid scope 1 is inserted from under the xiphoid process S into the pericardial cavity C created between the heart H and the pericardium P that constitutes the pericardial sac, through a flexible sheath 2. The rigid scope 1 is an endoscope whose shaft of the insertion part is rigid.

Figure 2:
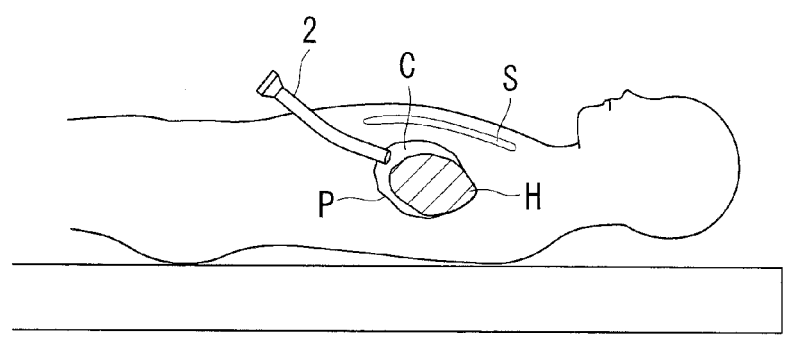
FIG. 2 is an illustration to explain a sheath insertion step according to one embodiment of the present invention.

Next, as shown in FIG. 2, a sheath insertion step (S1) is performed. In order to insert the sheath 2 into the pericardial cavity C, firstly, the pericardium P is penetrated with a puncture needle and the needle is inserted in the pericardial cavity C. Next, a thin and flexible guide wire 4 which is radiographically visible is inserted into the pericardial cavity C through the inside of the puncture needle. Next, the sheath 2 equipped with a dilator is inserted into the pericardial cavity C along the guide wire 4. When the distal end of the sheath 2 reaches the target position inside the pericardial cavity C, the dilator and the guide wire 4 are withdrawn and detached while leaving the sheath 2 behind. By so doing, the route from the hole (A) opened in the skin to the pericardial cavity is secured.

Figure 3:
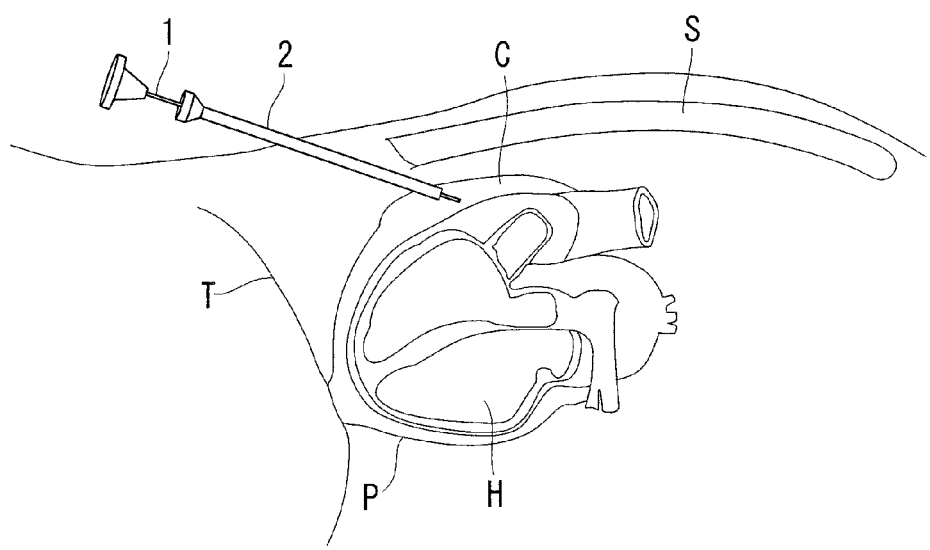
FIG. 3 is an illustration to explain a rigid scope insertion step according to one embodiment of the present invention.

Next, as shown in FIG. 3, a rigid scope insertion step (S2) is performed. The distal end of the rigid scope (endoscope) 1 is inserted into the pericardial cavity C through the sheath 2 that has been inserted in the pericardial cavity C directly in a subcutaneous manner according to the above-mentioned method without breaking the diaphragm T. At this time, since the flexible sheath 2 has been deformed by the surrounding tissue, the distal end of the straight shaped rigid scope 1 is inserted in the sheath 2 and is advanced into the pericardial cavity C while reforming the positions and the like of the surrounding tissue.

Figure 4:
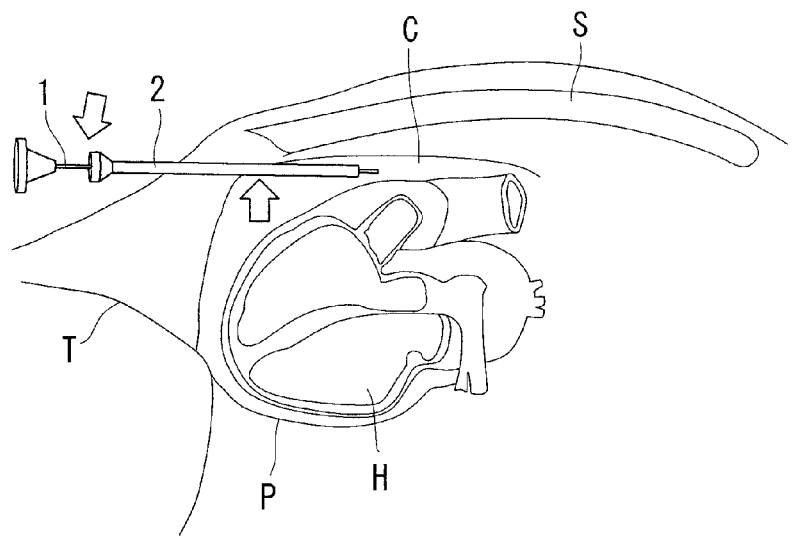
FIG. 4 is an illustration to explain a view field securing step according to one embodiment of the present invention.

Next, as shown in FIG. 4, a view field securing step (S3) is performed. The pericardium P is lifted up by the distal end of the rigid scope 1 with a vicinity of the xiphoid process S or the dorsal side of the sternum or an intercostal space acting as a fulcrum F, through the action such as pushing the hand-side unit (a part at the basal end) of the rigid scope 1 onto the abdomen. In this way, the space for securing a wide view field can be created inside the pericardial cavity C by pushing up the pericardium P with use of the rigid scope 1 itself, and thereby the anatomical positions of organs can be more clearly understood. In addition, it is possible, by observing the surface of the heart with the rigid scope 1, to observe the presence or absence of fat, the condition of the coronary arteries and the myocardium, the behavior of the heart H, the color, and the like.

Figure 5:
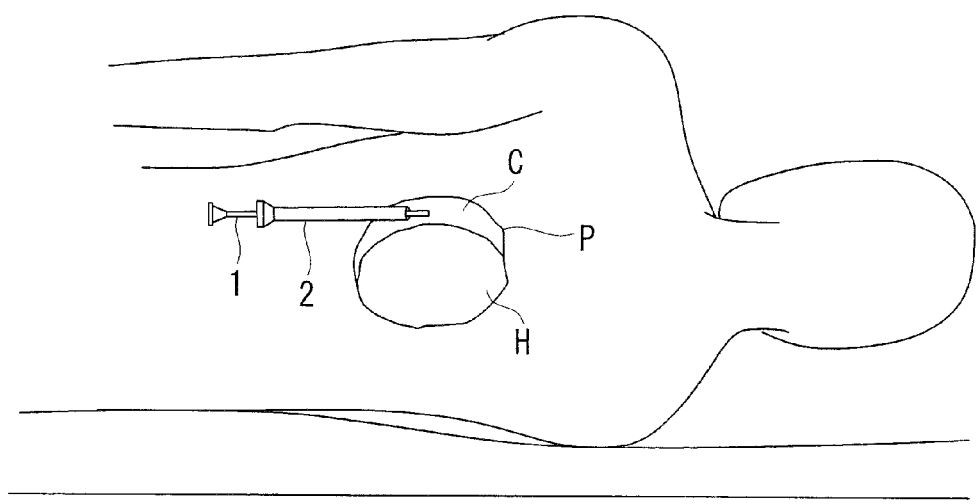
FIG. 5 is an illustration to explain a posture repositioning step according to one embodiment of the present invention.

Next, as shown in FIG. 5, a posture repositioning step (S4A) for securing the space on the left ventricle side is performed. By repositioning the body posture in the left lateral recumbent position, the position of the heart H is changed due to the force of gravity, by which a space can be secured in the pericardial cavity C between the left ventricle side of the heart H and the pericardium P. By so doing, the space for the view field on the left ventricle side can be secured. Also, the distal end of the rigid scope 1 can be kept from being dipped below a liquid level due to a liquid that has been pooled in the pericardial cavity C.

Figure 6:
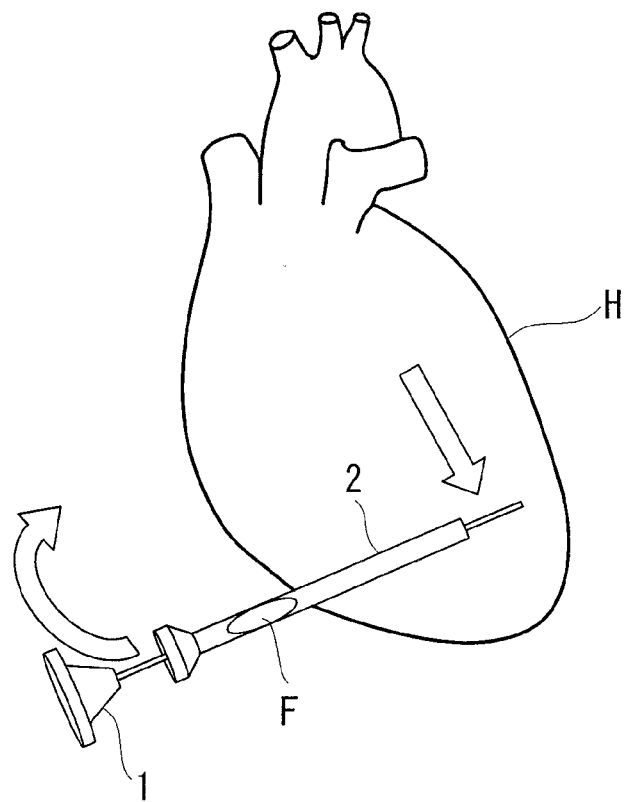
FIG. 6 is an illustration to explain a guide step according to one embodiment of the present invention.

Next, as shown in FIG. 6, a step to guide the rigid scope 1 to the lateral wall of the left ventricle (S5A) is performed. The distal end of the rigid scope 1 is slowly moved along the heart H within the space created on the left ventricle side of the pericardial cavity C (insertion step). At this time, the rigid scope 1 is moved while rotating clockwise with the insertion part of the sheath 2 acting as a fulcrum F (rotation step) with care so as not to lift up the pericardium P too much by the distal end of the rigid scope 1. By lifting up the pericardium P on the left ventricle side, the right atrium which is located on the opposite side across the heart H might be possibly compressed by the pericardium in the vicinity of the right atrium. Thus, the operation must be carefully performed while paying particular attention to the hemodynamic status. If the above-mentioned operation is performed quickly, the hemodynamic status might be deteriorated. Thus, the tension must be applied slowly so as not to rapidly interrupt the function of the heart H. The insertion step and the rotation step mentioned above may be performed at the same time.

By so doing, the space for the view field can be secured. In addition, a tented state of the pericardium P is created because the distal end of the rigid scope 1 is lifting up the pericardium P. Therefore, it is possible, by slowly moving the distal end, to operate the rigid scope 1 while observing the heart H as well as dispersing the tension.

Figure 7:
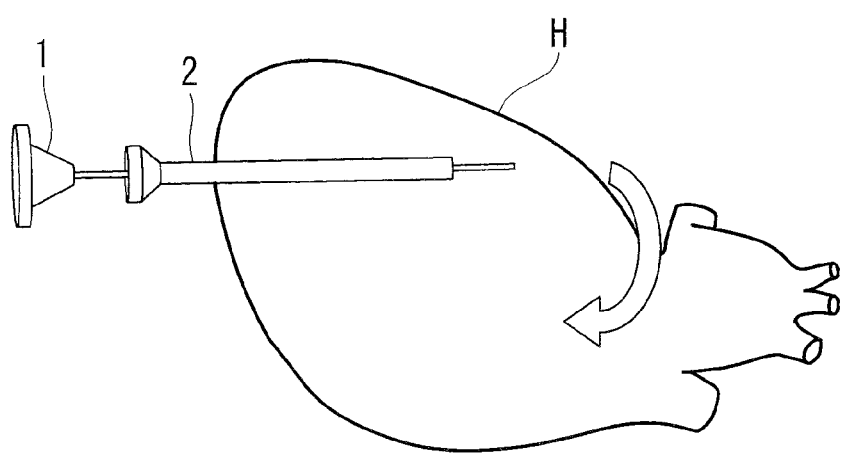
FIG. 7 is an illustration to explain a guide step according to one embodiment of the present invention.

Next, as shown in FIG. 7, a step to guide the rigid scope 1 to the posterior side of left ventricle (S5B) is performed. The distal end of the rigid scope 1 is further inserted in the direction to the left atrium along the heart wall, while slowly pushing the lateral wall of the left ventricle to the right ventricle side (downside) with the distal end of the rigid scope 1. As the pericardium P is adhered to a periphery of the pulmonary veins near the left atrium, the pulmonary veins are exposed by pushing and opening up between the heart H and the pericardium P, which are tightly attached to each other, with use of the shaft of the rigid scope 1. By so doing, the pulmonary veins on the posterior side of the heart H can be observed. In addition, atrial fibrillation ablation that will be described later can be conducted while observing the heart H by utilizing the pulmonary veins as landmarks.

Figure 8:
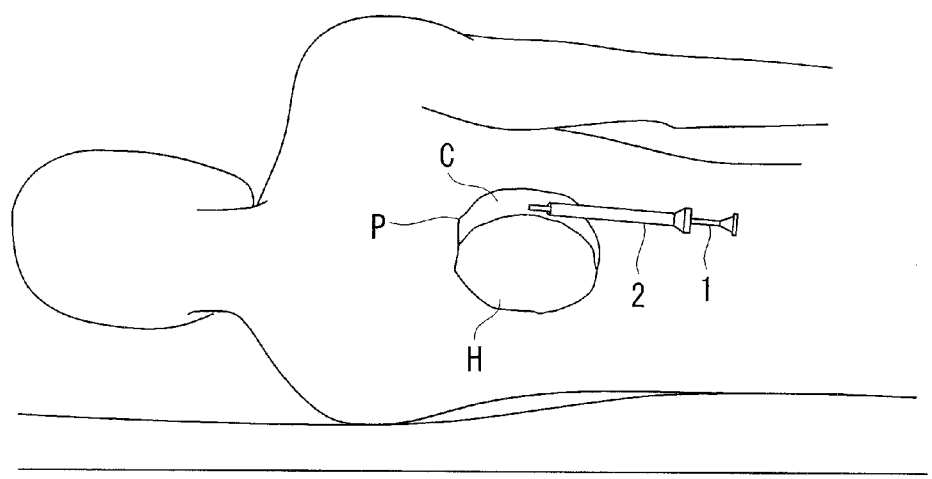
FIG. 8 is an illustration to explain a posture repositioning step according to one embodiment of the present invention.

Next, as shown in FIG. 8, a posture repositioning step (S4B) for securing the space on the right ventricle side is performed. By repositioning the body posture in the right lateral recumbent position, the position of the heart H is changed due to the force of gravity, by which a space can be secured in the pericardial cavity C between the right ventricle side of the heart H and the pericardium P. By so doing, the space for the view field on the right ventricle side can be secured.

Figure 9:
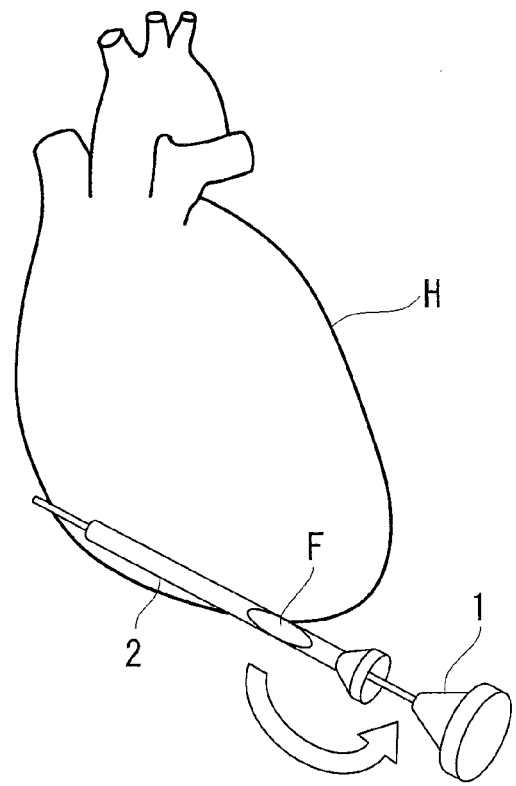
FIG. 9 is an illustration to explain a guide step according to one embodiment of the present invention.

Next, as shown in FIG. 9, a step to guide the rigid scope 1 to the lateral wall of the right ventricle (S5C) is performed. The distal end of the rigid scope 1 is slowly moved along the heart H within the space created on the right ventricle side of the pericardial cavity C (insertion step). At this time, the rigid scope 1 is moved while rotating anticlockwise with the insertion part of the sheath 2 acting as a fulcrum F (rotation step) with care so as not to lift up the pericardium P too much by the distal end of the rigid scope 1. The distal end portion of the rigid scope 1 is moved to the posterior side of the right ventricle with care so as not to push the shaft of the rigid scope 1 onto the right atrium. The insertion step and the rotation step mentioned above may be performed at the same time.

By so doing, the space for the view field can be secured. In addition, a tented state of the pericardium P is created because the distal end of the rigid scope 1 is lifting up the pericardium P. Therefore, it is possible, by slowly moving the distal end, to operate the rigid scope 1 while observing the heart H as well as dispersing the tension.

Figure 10:
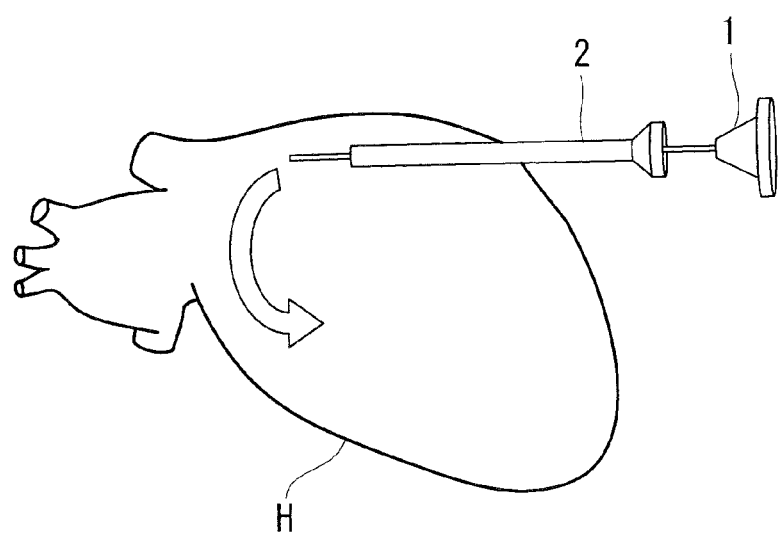
FIG. 10 is an illustration to explain a guide step according to one embodiment of the present invention.

Next, as shown in FIG. 10, a step to guide the rigid scope 1 to the left atrium (S5D) is performed. The distal end is further inserted in the posterior side of the heart (the direction to the left atrium) along the heart wall, while slowly pushing the lateral wall of the right ventricle to the base side (upside) with the distal end of the rigid scope 1. As the pericardium P is adhered to a periphery of the pulmonary veins near the left atrium, the pulmonary veins are exposed by pushing and opening up between the heart H and the pericardium P, which are tightly attached to each other, with use of the distal end portion of the shaft of the rigid scope 1. By so doing, the pulmonary veins on the posterior side of the heart H can be observed. In addition, atrial fibrillation ablation that will be described later can be conducted while observing the heart H by utilizing the pulmonary veins as landmarks.

Figure 11:
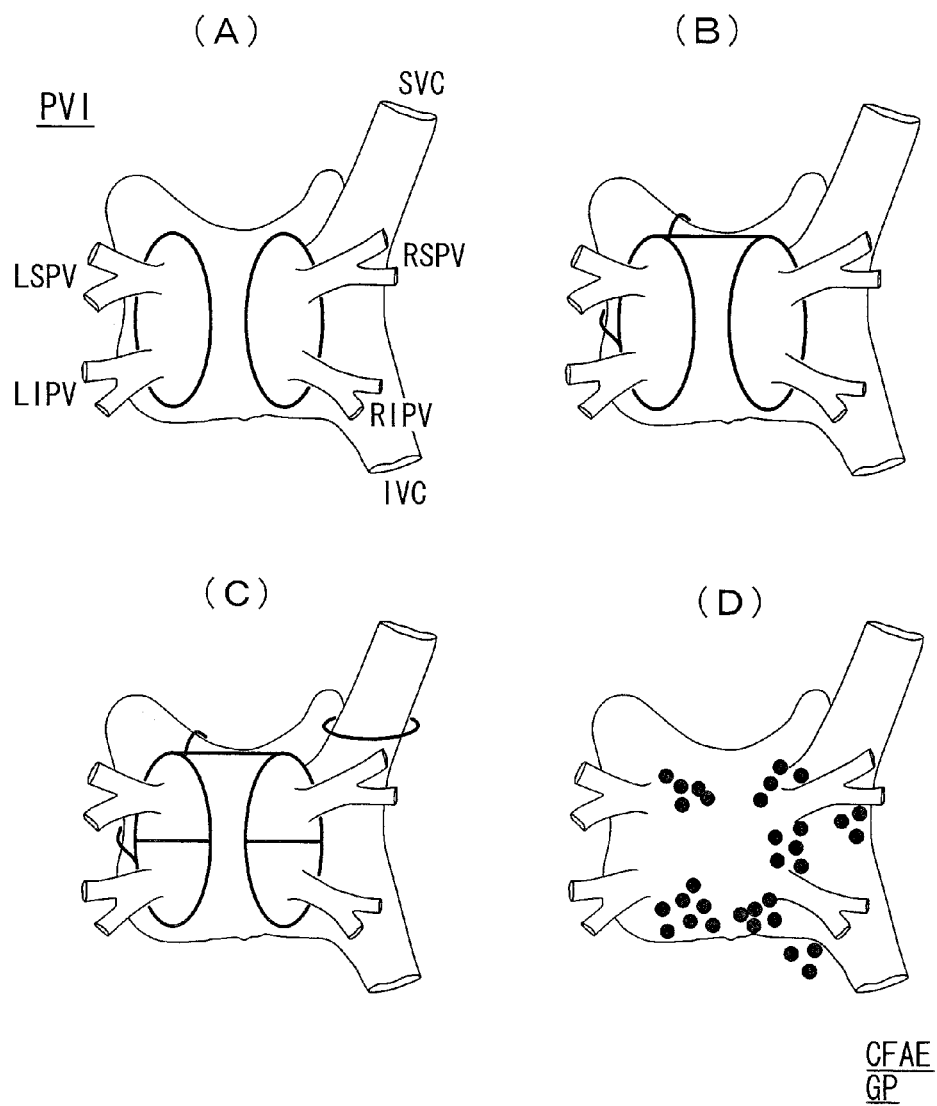
FIG. 11 is an illustration showing an ablation step according to this embodiment.

Next, an ablation step (S6) is performed. An ablation device (ablation catheter) 3 is inserted from the same open space being used for the sheath 2, and the surgical site is treated under observation. The ablation device 3 may be flexible, rigid, or semi-rigid. When the rigid scope 1 is moved, the ablation device 3 follows the movement. The position and the method of the ablation are as of a predetermined manner as shown in FIG. 11, and mapping may also be adopted together.

Figure 12:
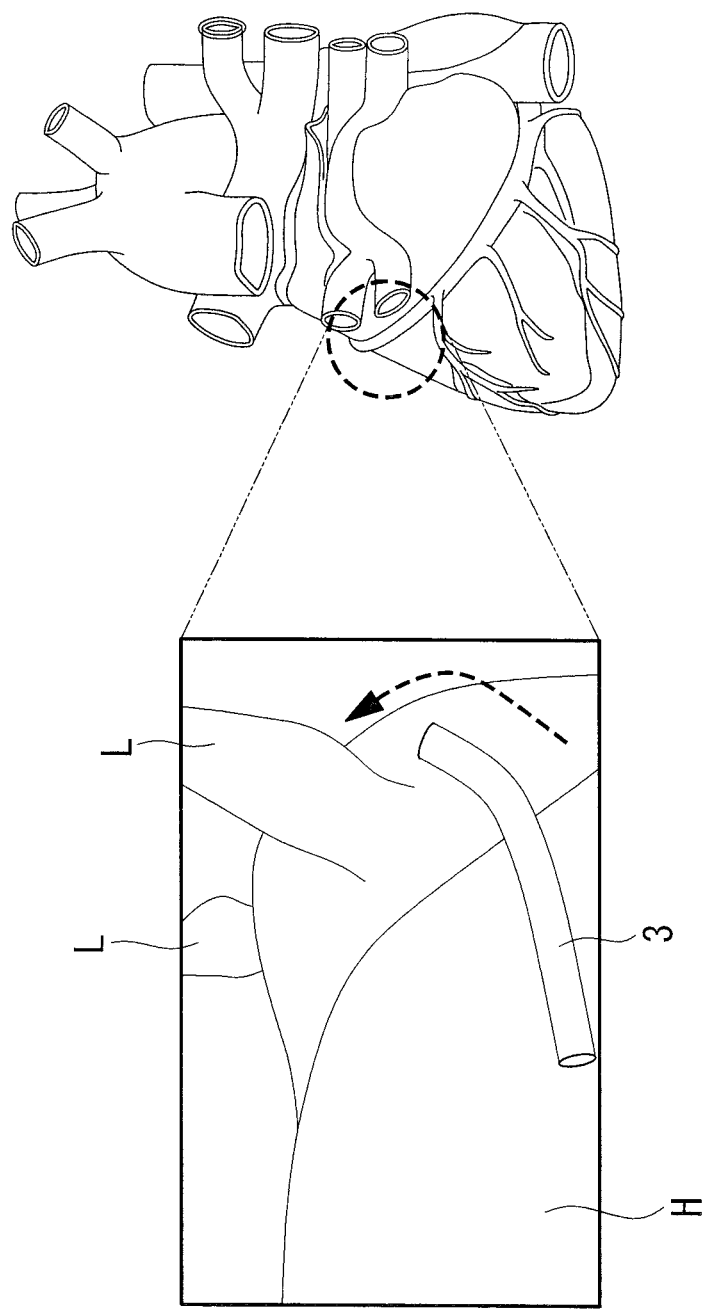
FIG. 12 is an illustration showing the ablation step according to this embodiment.

By so doing, the position to be treated can be understood with the rigid scope 1. Thus, the mapping is not always necessary any more, and therefore the surgery time can be shortened. It is possible to check by observing the endoscopic image as shown in FIG. 12, regarding whether or not the ablation device 3 is in touch with any tissue such as the left pulmonary veins L, whether or not the cauterization has been reliably completed, and whether or not any major vessel is damaged.

Figure 13:
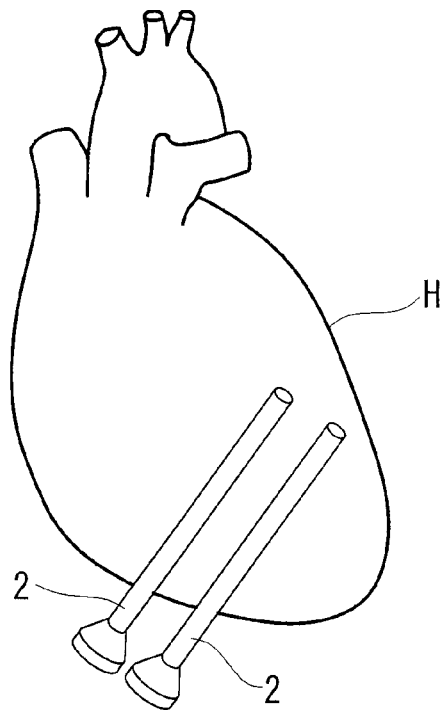
FIG. 13 is an illustration showing a modified example of the ablation step.

As shown in FIG. 13, in a modified example of the ablation step (S6), it is also possible to insert the rigid scope 1 and the ablation device 3 into the pericardial cavity C respectively from two sheaths 2 that have been inserted on the left and right. By so doing, a plurality of (two) small holes are opened, which is less invasive than opening one big hole. This can make it easy to close the puncture in the pericardium P.

Figure 14:
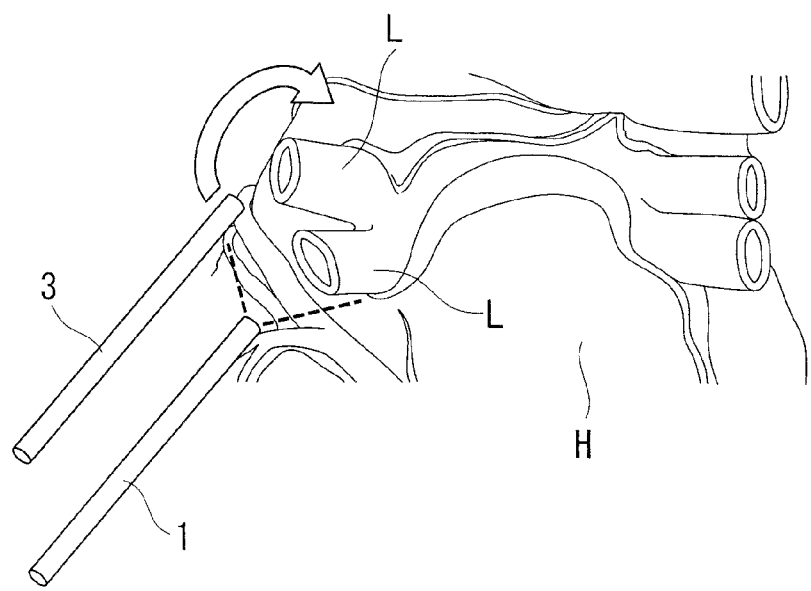
FIG. 14 is an illustration showing the modified example of the ablation step.
Figure 15:
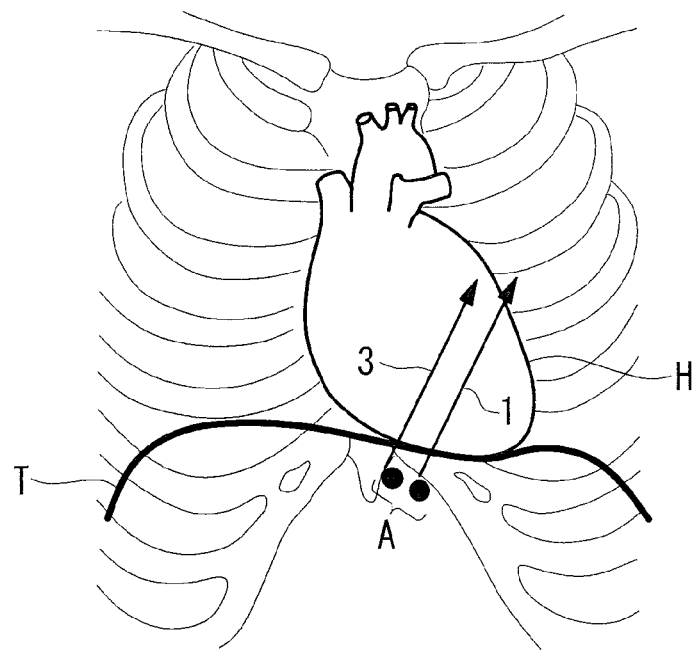
FIG. 15 is an illustration showing the modified example of the ablation step.
Figure 16:
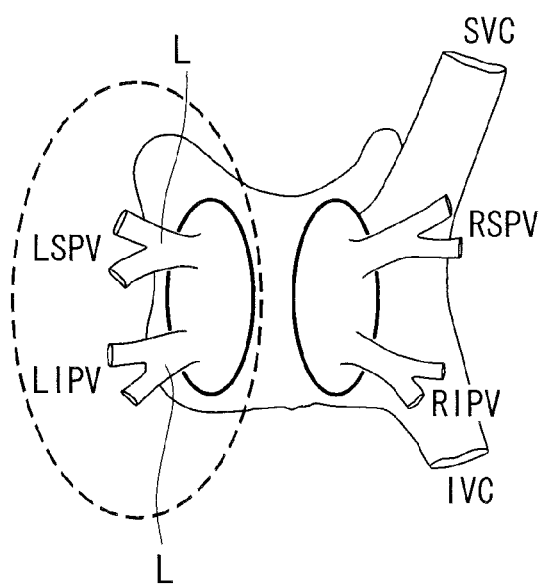
FIG. 16 is an illustration showing the modified example of the ablation step.

As shown in FIG. 14 to FIG. 16, next is a description of a case of ablation (isolation) of a periphery of the superior side of the left pulmonary veins L in the modified example of the ablation step (S6). In a case as shown in the FIG. 14 where the superior side of the left pulmonary veins L is to be isolated from the posterior side of the heart H, the rigid scope 1 is disposed in the sheath 2 on the right side of FIG. 13 and the ablation device 3 is inserted in the sheath 2 on the left side of FIG. 13. While looking at the two left pulmonary veins L with the rigid scope 1, the ablation of the left superior pulmonary vein (LSPV) is conducted with the ablation device 3 on the left side. If the ablation of the left inferior pulmonary vein (LIPV) is to be conducted in this state, the rigid scope 1 and the ablation device 3 would cross over each other, and thereby these devices would interfere with each other. This makes it difficult to perform the operation.

Figure 17:
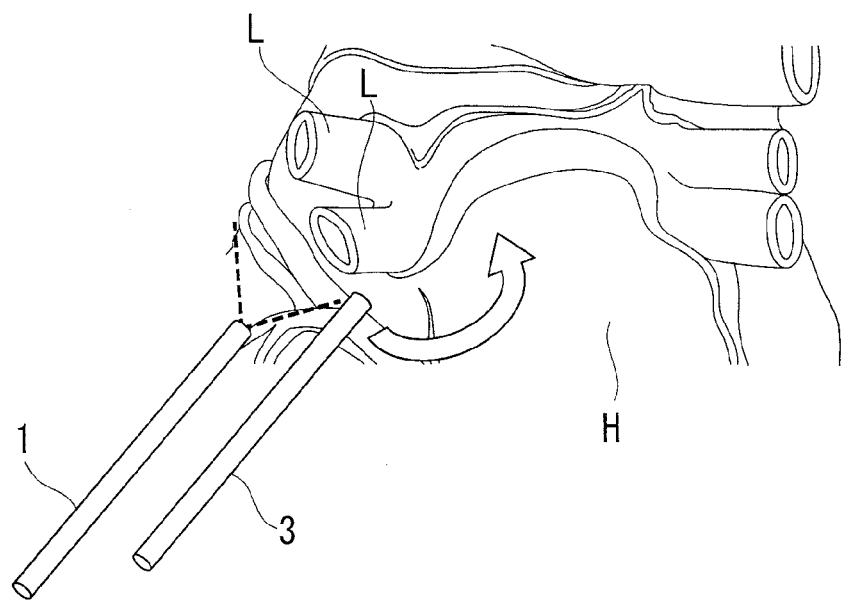
FIG. 17 is an illustration showing a modified example of the ablation step.
Figure 18:
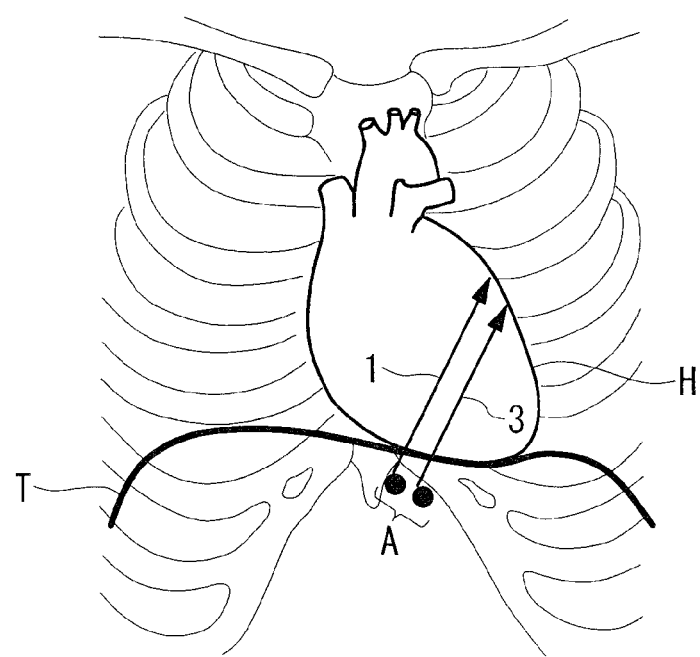
FIG. 18 is an illustration showing the modified example of the ablation step.

As shown in FIG. 17 and FIG. 18, next is a description of a case of ablation of a periphery of the inferior side of the left pulmonary veins L. In a case as shown in the FIG. 17 where the inferior side of the left pulmonary veins L is to be ablated from the posterior side of the heart H, the rigid scope 1 is disposed in the sheath 2 on the left side of FIG. 13 and the ablation device 3 is inserted in the sheath 2 on the right side of in FIG. 13. While looking at the two left pulmonary veins L with the rigid scope 1, the ablation of the left inferior pulmonary vein (LIPV) is conducted with the ablation device 3 on the right side. If the ablation of the left superior pulmonary vein (LSPV) is to be conducted in this state, the rigid scope 1 and the ablation device 3 would cross over each other, and thereby these devices would interfere with each other. This makes it difficult to perform the operation.

The same procedure is taken for the case of ablation of a periphery of the right pulmonary veins (here, details are not described).

Figure 19:
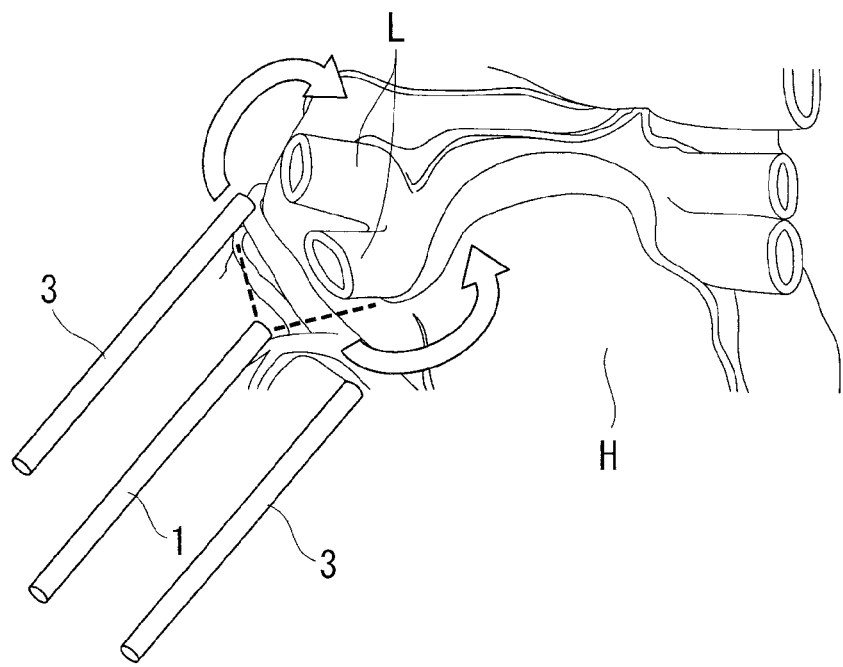
FIG. 19 is an illustration showing a modified example of the ablation step.
Figure 20:
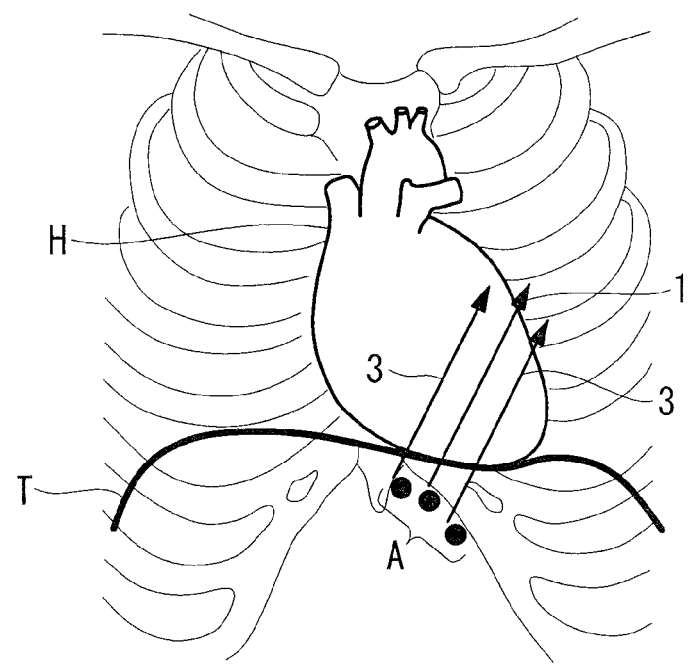
FIG. 20 is an illustration showing the modified example of the ablation step.

As shown in FIG. 19 and FIG. 20, next is a description of a case of ablation of the left pulmonary veins L with use of two ablation devices 3. Three sheaths 2 are inserted in the pericardial cavity C on the left, right, and center. The rigid scope 1 is disposed in the central sheath 2 and the ablation devices 3 are inserted respectively in the sheaths 2 disposed on the left side and the right side.

The same procedure is taken for the case of ablation of a periphery of the right pulmonary veins with use of two ablation devices (here, details are not described).

Figure 21:
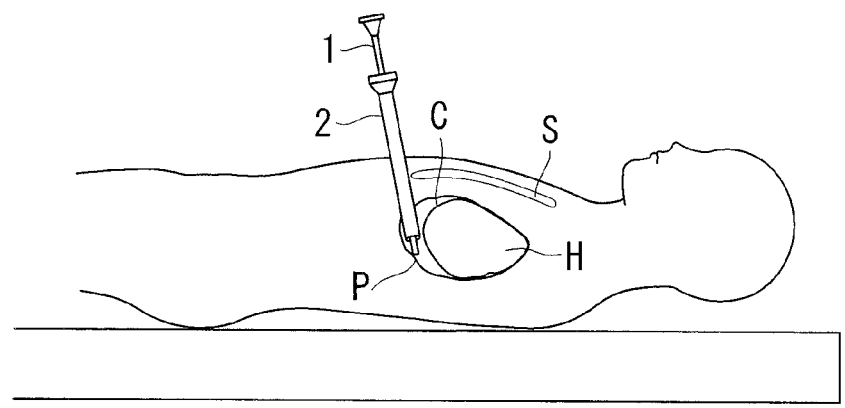
FIG. 21 is an illustration showing a modified example of the rigid scope insertion step and the view field securing step.
Figure 22:
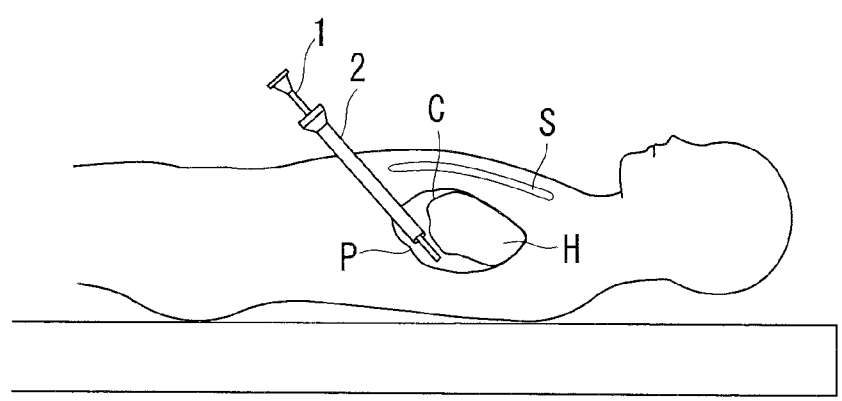
FIG. 22 is an illustration showing a modified example of the rigid scope insertion step and the view field securing step.
Figure 23:
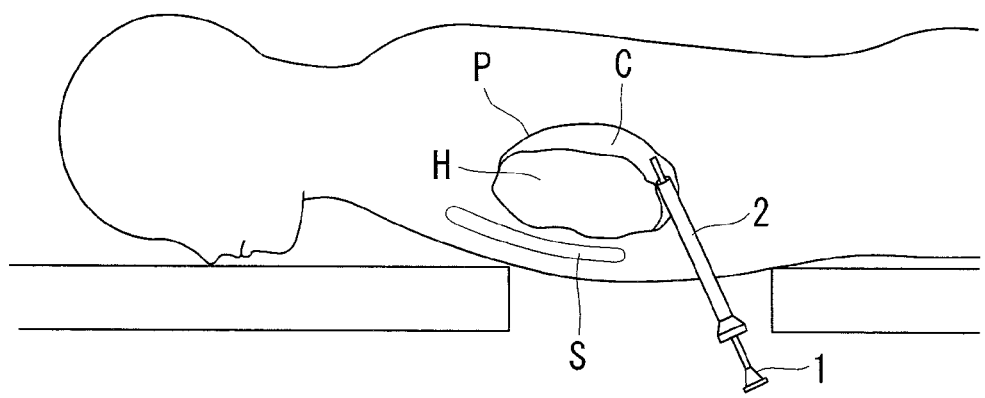
FIG. 23 is an illustration showing a modified example of the rigid scope insertion step and the view field securing step.

As shown in FIG. 21, in a modified example of the rigid scope insertion step (S2) of FIG. 3 and the view field securing step (S3) of FIG. 4, an approach is made from the xiphoid process S in a direction from the apex to the posterior side of the heart. First, the rigid scope 1 is inserted through the sheath 2 along the diaphragm T. Next, the rigid scope 1 is inserted until the distal end of the rigid scope 1 passes by the apex, and the posterior side of left ventricle is observed. At this time, as shown in FIG. 22, the heart H may also be pushed up to the upside with the shaft of the rigid scope 1. By so doing, the view field for the surgical site can be secured. Then, the left atrium is reached by the distal end of the rigid scope 1. By so doing, the posterior side of the heart H can be reached without passing by the left coronary artery (anterior descending coronary). Thus, the operation can be safely conducted. Alternatively, as shown in FIG. 23, the patient may be laid on his/her face so that the posterior side of the heart is oriented upward.

Figure 24:
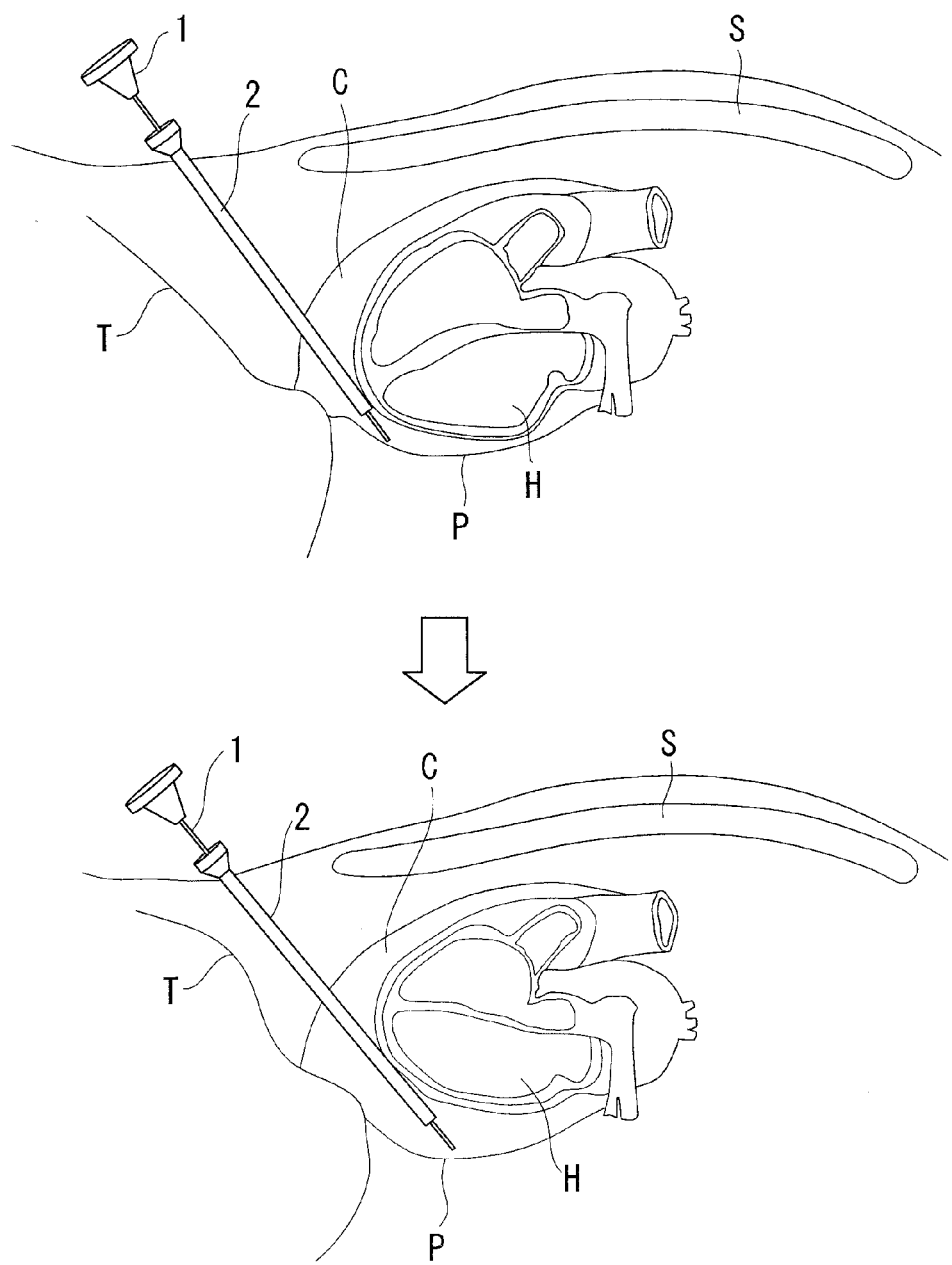
FIG. 24 is an illustration showing another modified example of the view field securing step.

As shown in FIG. 24, in a modified example of the view field securing step (S3) of FIG. 4, the rigid scope 1 is gradually advanced forward while repeating the action of inserting the distal end of the rigid scope 1 into the space between the heart H and the pericardium P (insertion step) and the action of lifting up the heart H with the shaft of the rigid scope 1. That is to say, the heart H is lifted up by the operation to push the shaft of the rigid scope 1 onto the heart side in a state where the shaft is being disposed on a tangential direction of the heart H (pushing step). The view field can be developed by lifting up the heart H with the shaft of the rigid scope 1.

The insertion step and the pushing step mentioned above may be performed at the same time. It is also possible to use a sheath having a rigid portion ranging from the hand-side unit to a position until which the rigid scope 1 can be inserted, instead of the above-mentioned flexible sheath 2.

At this time, care must be taken so as not to push the heart H with the distal end of the rigid scope 1. Even if a space for the target site can be secured within the pericardial cavity C by the posture repositioning step (S4), in a case where the heart H has felt down to the vertical direction due to the force of gravity, there is no open space between the heart H and the pericardium P. Even in such a case, it is possible to effectively approach the site where there is no open space between the heart H and the pericardium P. In this way, the view field can be secured even in a case where repositioning the body posture is not enough to secure the view field.

Figure 25:
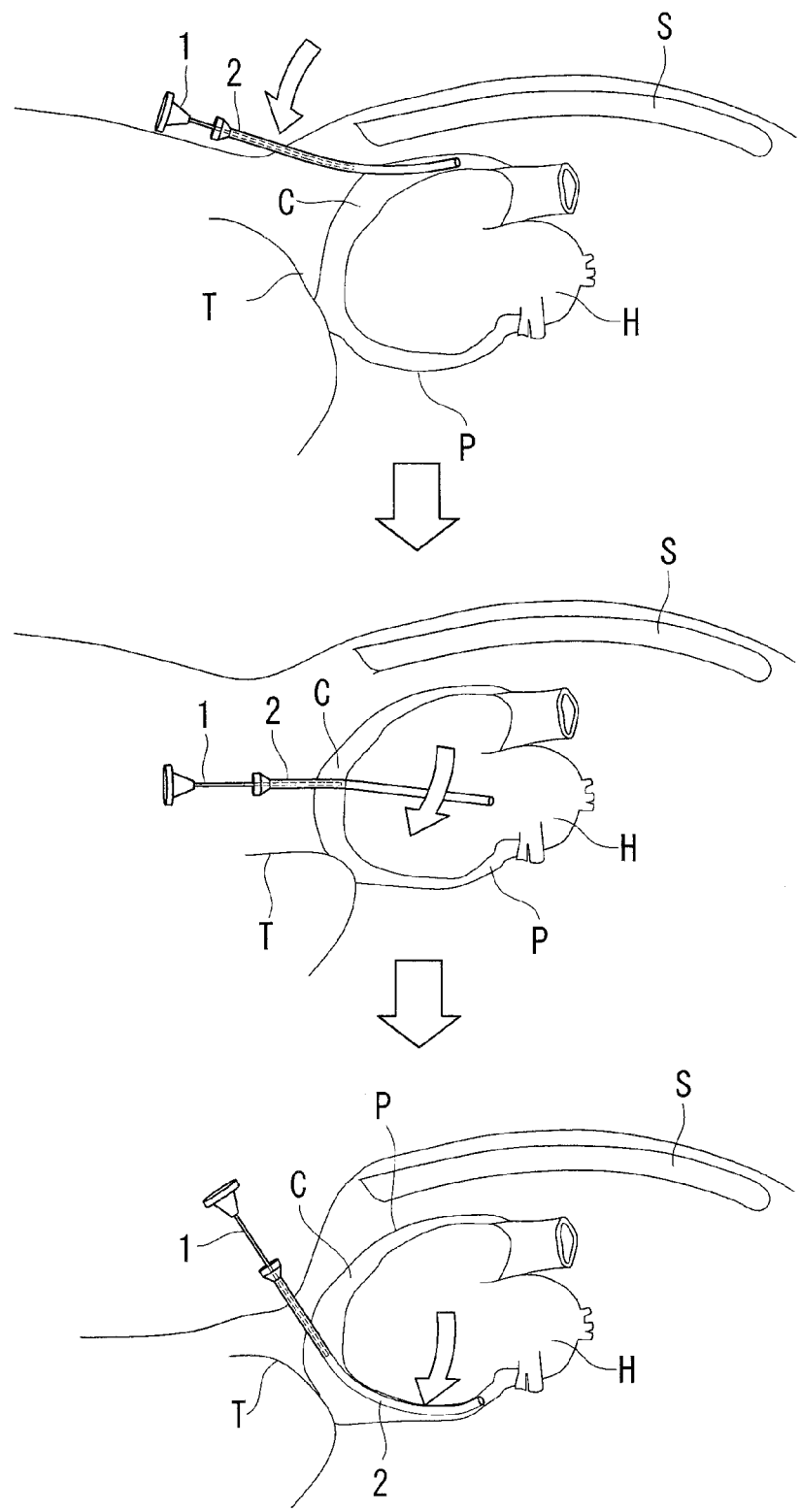
FIG. 25 is an illustration showing another modified example of the view field securing step.

As shown in FIG. 25, in another modified example of the view field securing step (S3) of FIG. 4, all the surrounding organs (organs other than bones such as the heart, the lung, the stomach, the liver, the esophagus, the diaphragm, and the pericardium) around the route to insert the rigid scope 1 from the xiphoid process S to the pericardial cavity C are soft and quite freely movable. Accordingly, by pushing the rigid scope 1 onto the abdomen, the rigidity of the shaft of the rigid scope 1 can be utilized to exclude the surrounding organs around the insertion route and to adjust the angle and the position of the route to insert the rigid scope 1.

Specifically, firstly, the rigid scope 1 is inserted to a middle of the sheath 2 in a state where the flexible sheath 2 is inserted deep inside the anterior wall of the pericardial cavity C. The depth of the insertion should be checked by seeing the place around where the distal end of the rigid scope 1 has been little inserted into the pericardial cavity C through X-ray radioscopy or the like. Regarding the depth to insert the rigid scope 1, it is either possible that the distal end of the rigid scope 1 is inserted deep inside the pericardial cavity C or not inserted in the pericardial cavity C.

In this state, the operation unit of the rigid scope 1 is held in the right hand and the shaft of the rigid scope 1 is held in the left hand, and the whole rigid scope 1 is pushed onto the abdomen. By so doing, the insertion route itself from the xiphoid process S to the pericardium P is displaced to the direction where the force has been applied (downward). Next, the sheath 2 and the rigid scope 1 that has been inserted as a cored bar to a middle of the sheath 2 are operated horizontally and vertically while pushing onto the abdomen. In this way, the insertion part of the sheath can be moved by utilizing the softness and flexibility of the soft sheath 2. Next, the flexible sheath 2 being inserted in the pericardial cavity C is allowed to pass by the lateral side of the left ventricle or the right ventricle slidably over the surface of the heart H. While pushing the shaft of the rigid scope 1 acting as the cored bar onto the abdomen, the rigid scope 1 is operated until the distal end of the rigid scope 1 reaches the posterior side of the heart H (the posterior side wall of the left ventricle).

By so doing, even if the sheath 2 is inserted in the anterior wall, it is readily possible to turn it around to the posterior side of the heart H, and to readily change the route to insert the sheath 2 without largely compressing the heart H. Therefore, the posterior side of the heart H can be reached by the rigid scope 1. It is sometimes possible for the sheath 2 being inserted in the anterior wall of the heart H, to turn around to the posterior side of the heart H only by changing the angle to insert the rigid scope 1.

An attention must be paid to carefully check the position through X-ray radioscopy while checking the hemodynamic status at all times, and so as not to compress organs other than the heart H too much. A holder arm for holding the rigid scope 1 may also be adopted so as to alleviate the burden on the operator. In addition, a pressure sensor or a means to monitor the distance to push may also be additionally used so as not to push the abdomen too much.

Figure 26:
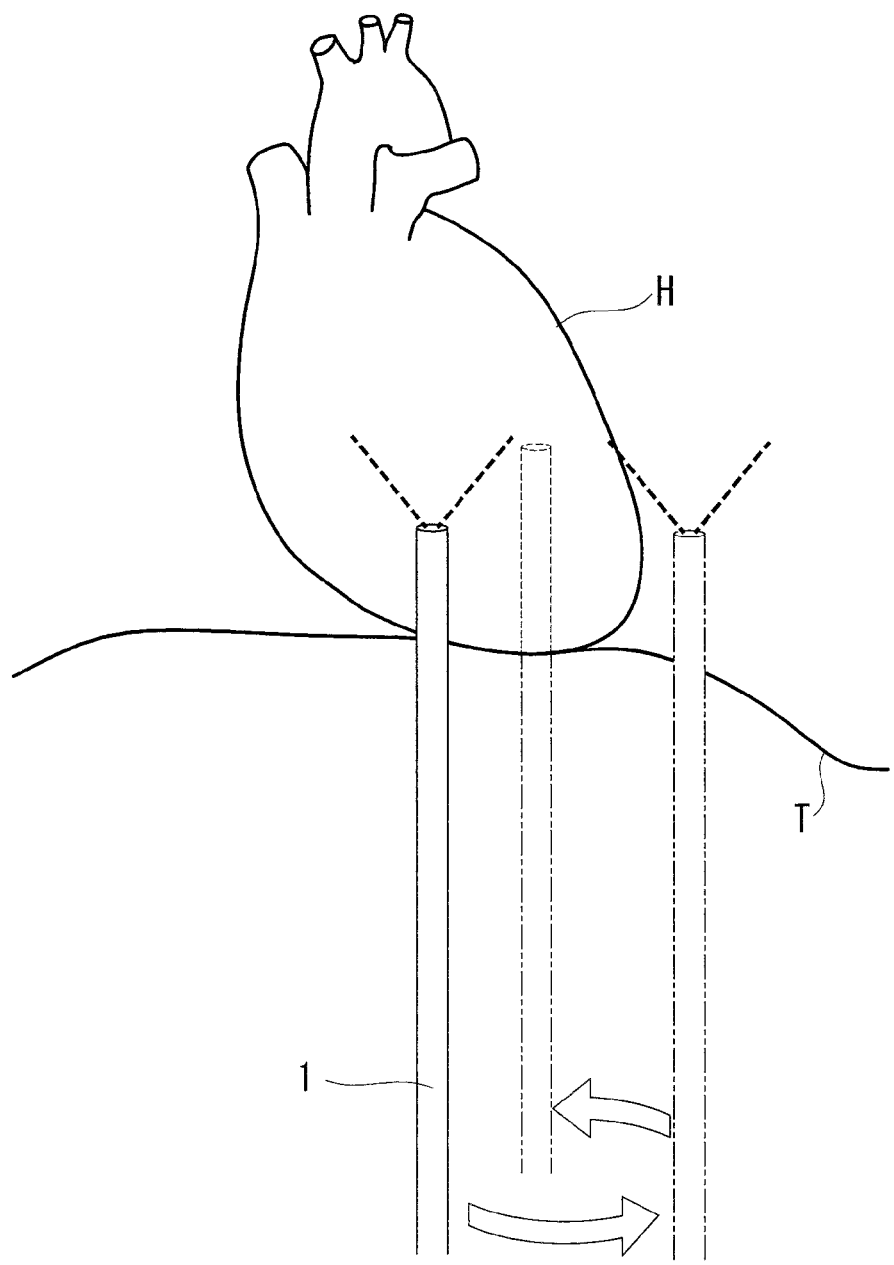
FIG. 26 is an illustration showing another modified example of the view field securing step.

As shown in FIG. 26, in yet another modified example of the view field securing step (S3) of FIG. 4, in a state where the sheath 2 and the rigid scope 1 are inserted in the anterior wall of the pericardial cavity, the operation unit of the rigid scope 1 is held in the right hand and the shaft of the rigid scope 1 is held in the left hand, and the whole rigid scope 1 is pushed onto the abdomen. Then, the insertion route itself from the xiphoid process S to the pericardium P is displaced downward. While pushing the hand-side operation unit of the rigid scope 1 onto the abdomen, the hand-side operation unit itself of the rigid scope 1 is moved parallelly toward the left ventricular side. At this time, the insertion part is moved along the surface of the heart H with care so as not to compress the heart H too much by the shaft of the rigid scope 1 inside the pericardial cavity C. The shaft of the rigid scope 1 is moved parallelly from the lateral wall of the left ventricle to the posterior side through the operation of the hand-side operation unit of the rigid scope 1.

By so doing, it is possible to move from the anterior wall to the posterior side wall while checking the pericardial cavity C with the rigid scope 1. In addition, it is possible to readily turn around to the posterior side of the heart H from the state where the sheath is inserted in the anterior wall.

In yet another modified example of the view field securing step (S3) of FIG. 4, an operation to open the site of adhesion between the heart H and the pericardium P is conducted by inserting the rigid scope 1 into the pericardial cavity C and using dissection forceps 6 that have been inserted through the same sheath 2 or another sheath 2, that is, one of a plurality of sheaths 2 inserted from a different route. The dissection forceps 6 are inserted between the pericardium P and the heart H under the rigid scope 1, and operated while observing the distal end portion of the dissection forceps 6. The operation to open the jaw of the catcher unit of the dissection forceps 6 so as to open up between the heart H and the pericardium P and to rotate the jaw of the dissection forceps 6 is repeated. An antiadhesive agent or a seal to prevent pericardial adhesion may also be put on.

An approach is made to the left or right pulmonary veins by entering the posterior side of the heart H by the above-mentioned method. Using a surgical instrument for ablation, the base of the pulmonary veins is lightly pushed with the distal end of the surgical instrument, by which the distal end portion of the surgical instrument for ablation can be disposed on the atrium part around the base of the pulmonary veins. The periphery of the pulmonary veins can be ablated by applying energy to this distal end portion. For example, it is possible to conduct RF (radiofrequency) ablation, cryoablation, photoablation, or the like.

Figure 27:
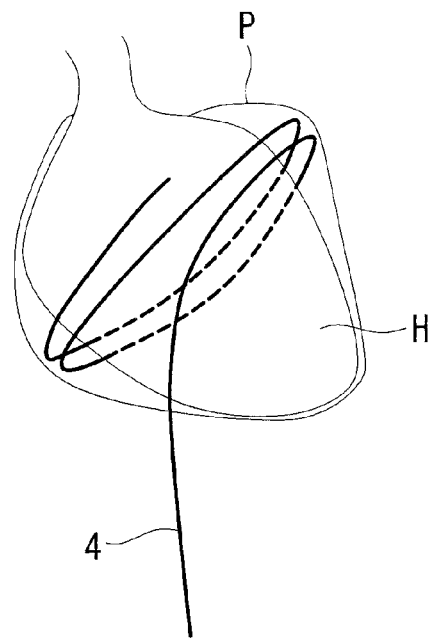
FIG. 27 is an illustration showing another modified example of the view field securing step.

As shown in FIG. 27, in yet another modified example of the view field securing step (S3) of FIG. 4, the view field may also be secured with use of a guide wire (GW) 4. A slightly firm guide wire 4 is looped within the pericardial cavity C (for example, two or more rounds), and then is allowed to outspread like a spring to expand the pericardium P outward. By guiding the guide wire 4 in a direction to the view field of the rigid scope 1, the view field forward of the view field direction of the rigid scope 1 can be secured at all times. By so doing, the pericardium P which covers the heart H can be expanded outward by utilizing the force of the guide wire 4, which is embracing the heart H within the pericardial cavity C and is getting back to the initial straight form. By so doing, the view field of the rigid scope 1 can be secured.

Figure 28:
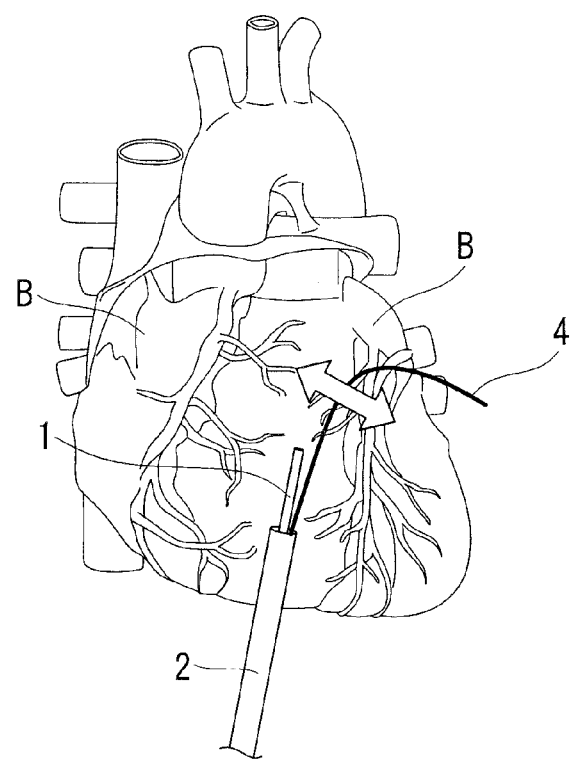
FIG. 28 is an illustration showing another modified example of the view field securing step.
Figure 29:
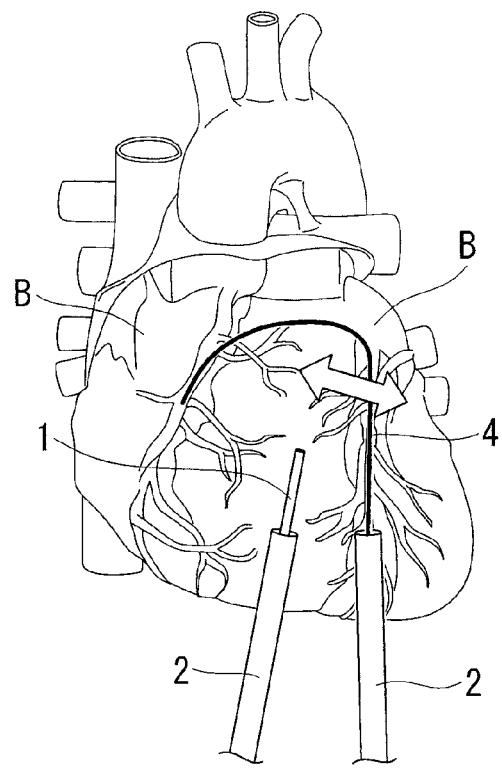
FIG. 29 is an illustration showing another modified example of the view field securing step.

In addition, as shown in FIG. 28 and FIG. 29, an organ inside the view field can be displaced or moved by the operation of horizontally and vertically shaking or rotating the guide wire 4 itself, or the sheath 2 inserted with the guide wire 4. The view field can be secured by this operation. Specifically, a wider view field can be secured by turning over the auricle B inside the view field with the guide wire 4. This can make it easy to observe vessels on the posterior side or the lateral sides of the auricle B, and the like. The guide wire 4 and the rigid scope 1 may be inserted in the same sheath 2, or may also be separately inserted from different routes with use of a plurality of sheaths 2. If these are inserted in the same sheath 2, the sheath 2 and the guide wire 4 are moved by moving the rigid scope 1. In this way, the view field can be secured by moving an organ within the pericardium P with use of the guide wire 4 like forceps.

Figure 30:
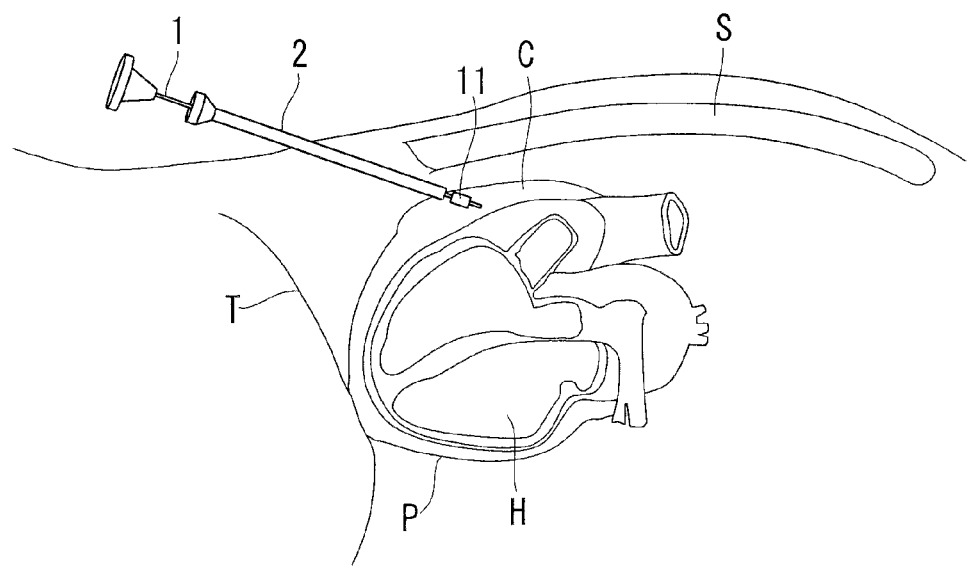
FIG. 30 is an illustration showing another modified example of the view field securing step.
Figure 31:
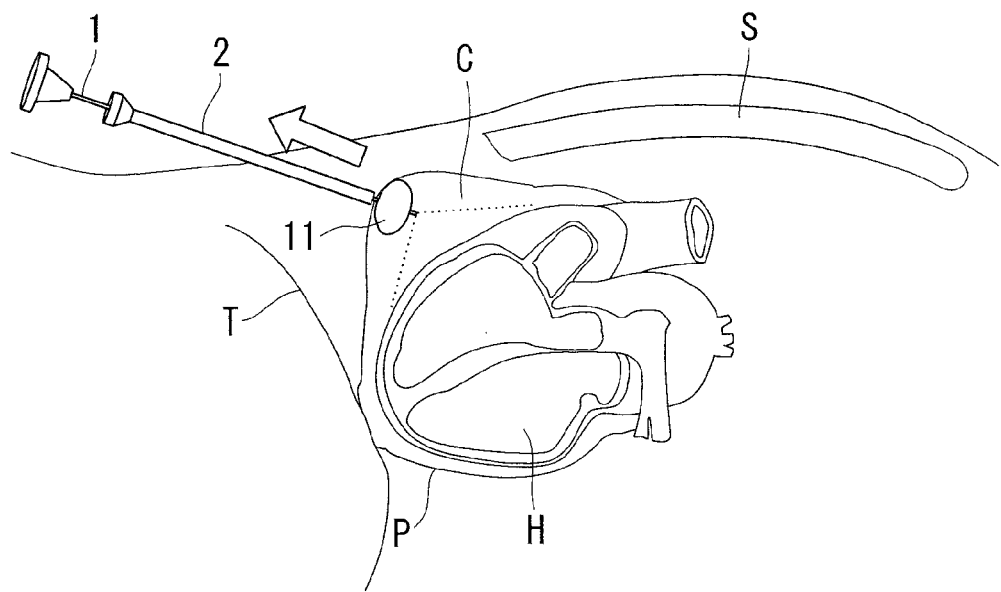
FIG. 31 is an illustration showing another modified example of the view field securing step.

As shown in FIG. 30 and FIG. 31, in another modified example of the view field securing step (S3) of FIG. 4, a balloon 11 may be provided on a distal end of the insertion part of the rigid scope 1. FIG. 30 shows a state in which the balloon 11 provided on the distal end of the insertion part of the rigid scope 1 is deflated. FIG. 31 shows a state in which the balloon 11 is inflated.

After inserting the rigid scope 1 in the pericardial cavity C, the balloon 11 in a deflated state is inflated with use of an insufflation lumen 12 (not shown). Then, as shown in FIG. 30, the basal end of the rigid scope 1 is pulled to thereby pull the inflated balloon 11 provided on the distal end of the insertion part of the rigid scope 1 in a direction outward from the body. By so doing, the pericardium P is hanged up by the inflated balloon 11, and the pericardium P is pulled apart from the heart H. Therefore, the open space of the pericardial cavity C is expanded, by which the view field can be secured.

This balloon 11 is configured so that it can be inflated in the entire circumferential direction. The insufflation lumen 12 for inflating the balloon 11 may be either inserted inside the rigid scope 1 or formed so as to fit along the outside of the insertion part of the rigid scope 1. In addition, it is also possible to adopt another type of inflatable unit but for a balloon, for example, a parasol-like unit that can be inflated in the radial direction, or a fixing means that can hold or suck the inside of the pericardium P (not shown).

So far, what has been conducted so as to secure a space for the view field is injection of gas in the pericardial cavity C, insertion of a balloon as a single unit, or such a manipulation. However, when it comes to the case of gas injection, it is difficult to secure a space for the view field in a vicinity of the apex, although it is possible to secure an upper space with respect to the gravity vector (mostly, the right ventricle side in the case of the dorsal position). Moreover, when it comes to the case of insertion of a balloon as a single unit, it has been difficult to reliably secure a space for the view field in a vicinity of the apex, because the position of the balloon is displaced due to the heartbeat of the heart H.

According to this embodiment, since the balloon 11 is provided on the distal end of the insertion part of the rigid scope 1, the balloon 11 can be pulled up by pulling the basal end of the rigid scope 1. By so doing, the open space of the pericardial cavity C is expanded by the balloon 11, and thus the distance between the rigid scope 1 and the apex is secured. Accordingly, a lower part of the anterior wall and a periphery of the apex of the heart H, which have been so far difficult to observe by a conventional method, can be reliably observed without an influence of the movement of the heart H.

Figure 32:
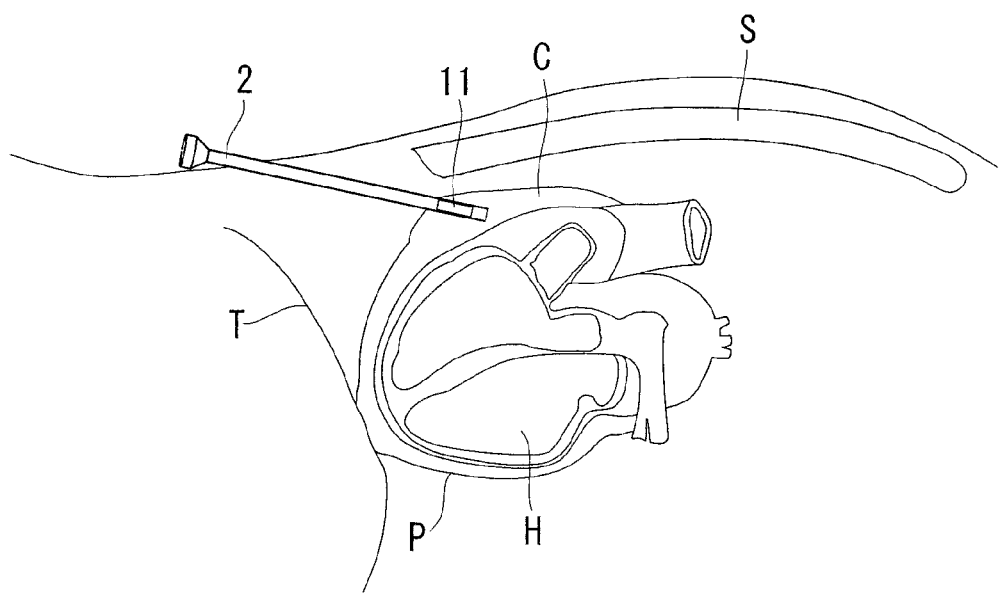
FIG. 32 is an illustration showing another modified example of the view field securing step.
Figure 33:
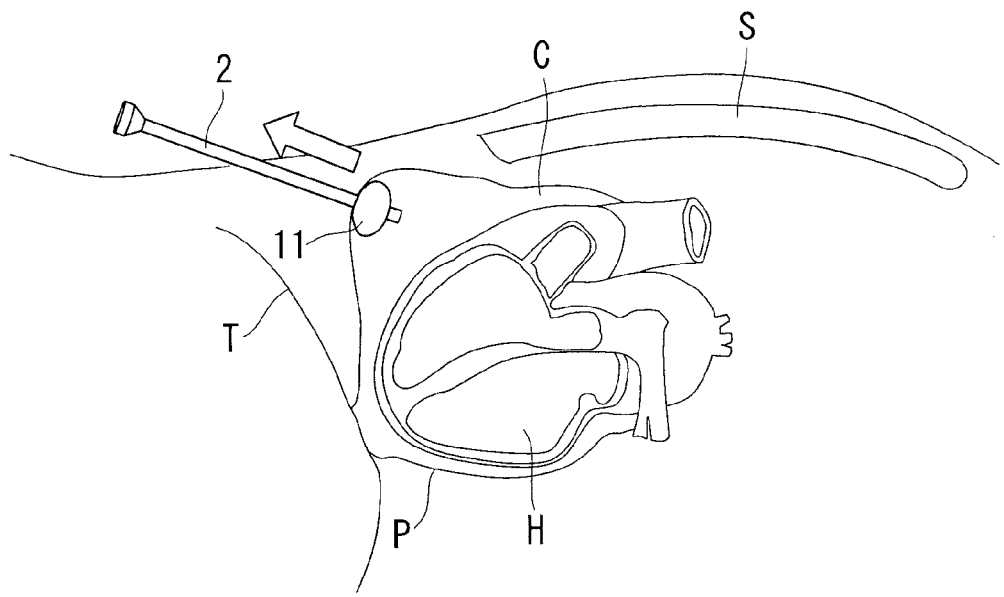
FIG. 33 is an illustration showing another modified example of the view field securing step.
Figure 34:
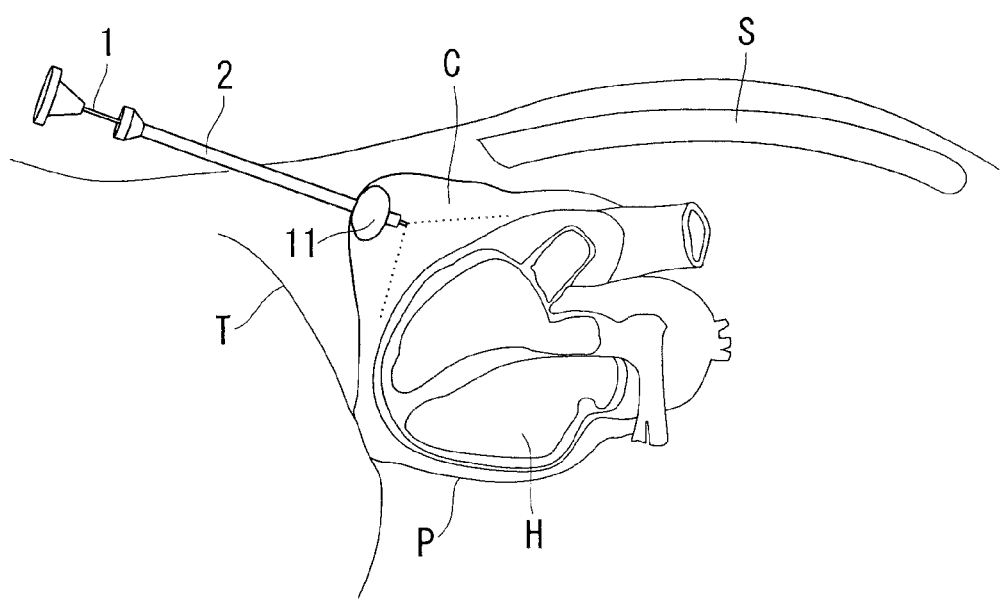
FIG. 34 is an illustration showing another modified example of the view field securing step.

As shown in FIG. 32 to FIG. 34, in another modified example of the view field securing step (S3) of FIG. 4, a balloon 11 may be provided on a distal end of the sheath 2. FIG. 32 shows a state in which the balloon 11 provided on the distal end of the sheath 2 is deflated. FIG. 33 shows a state in which the balloon 11 is inflated in the pericardial cavity C. FIG. 34 shows a state in which the heart H is being observed by inserting the rigid scope 1 after securing the view field with the inflated balloon 11.

After inserting the sheath 2 in the pericardial cavity C, the balloon 11 in a deflated state is inflated by supplying air through an insufflation lumen 12 (not shown). Next, the basal end of the sheath 2 is pulled to thereby pull the inflated balloon 11 provided on the distal end of the sheath 2 in a direction outward from the body. By so doing, the pericardium P is hanged up, and the pericardium P is pulled apart from the heart H. Therefore, the open space of the pericardial cavity C is expanded, by which the view field can be secured.

According to this embodiment, since the balloon 11 is provided on the distal end of the sheath 2, the balloon 11 can be pulled up by pulling the basal end of the sheath 2. By so doing, the distance between the distal end of the sheath 2 and the apex is secured. Therefore, the view field can be secured before inserting the rigid scope 1. In this way, a lower part of the anterior wall and a periphery of the apex of the heart H, which have been so far difficult to observe by a conventional method, can be reliably observed without an influence of the movement of the heart H. Moreover, the degree of freedom of the operation of the rigid scope 1 can be improved much better than the case of securing the view field with use of the rigid scope 1 itself.

Figure 35:
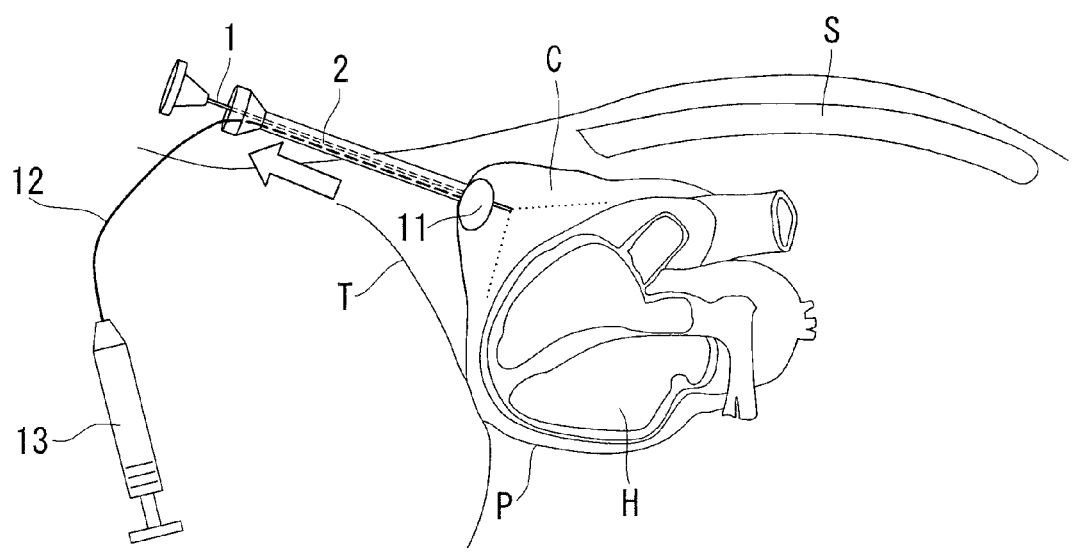
FIG. 35 is an illustration showing another modified example of the view field securing step.

As shown in FIG. 35, in another modified example of the view field securing step (S3) of FIG. 4, a balloon 11 that is a separate unit from the rigid scope 1 may be inserted with the rigid scope 1 in the pericardial cavity C through the sheath 2. After inserting the sheath 2 in the pericardial cavity C, the balloon 11 in a deflated state is inflated by supplying air from a syringe 13 through an insufflation lumen 12 which runs through the inside of the sheath 2. Then, the inflated balloon 11 is pulled in a direction outward from the body. By so doing, the pericardium P is hanged up, and the pericardium P is pulled apart from the heart H. Therefore, the open space of the pericardial cavity C is expanded, by which the view field can be secured.

According to this embodiment, since the balloon 11 is inserted in a separated manner from the rigid scope 1, the open space of the pericardial cavity C can be expanded by pulling up only this balloon 11 in a direction outward from the body through the insufflation lumen 12, by which the view field can be secured. For this reason, the rigid scope 1 can be moved forward and backward while pulling the inflated balloon 11 in a direction outward from the body. In this way, a lower part of the anterior wall and a periphery of the apex of the heart H, which have been so far difficult to observe by a conventional method, can be reliably observed without an influence of the movement of the heart H. Moreover, the degree of freedom of the operation of the rigid scope 1 can be improved much better than the case of securing the view field with use of the rigid scope 1 itself.

In this embodiment, the rigid scope 1 and the balloon 11 are inserted in the pericardial cavity C through one same sheath 2. However, instead of this, it is also possible to insert the rigid scope 1 and the balloon 11 in the pericardial cavity C, respectively through different sheaths 2.

Figure 36:
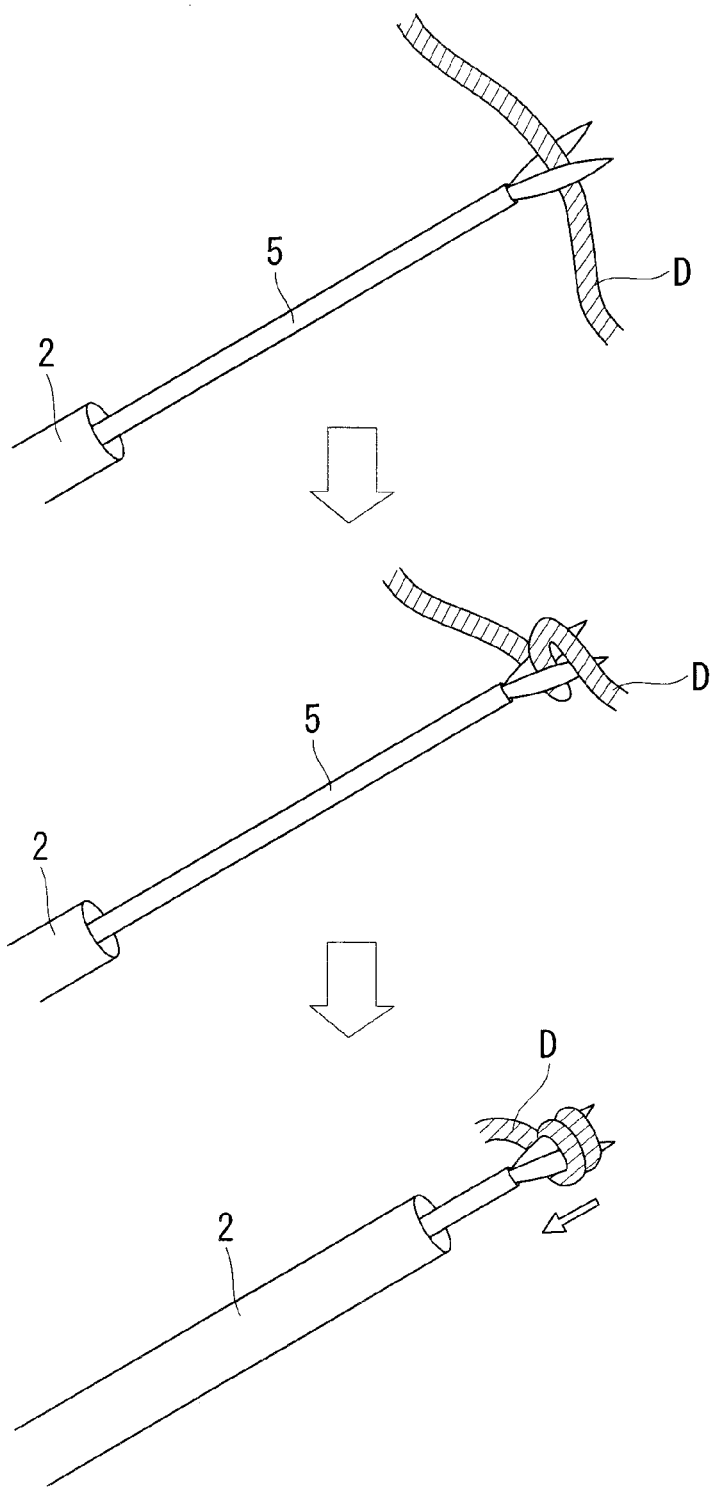
FIG. 36 is an illustration showing another modified example of the view field securing step.

As shown in FIG. 36, in yet another modified example of the view field securing step (S3) of FIG. 4, a clot may be removed by using holding forceps. If blood is retained in the pericardial cavity C, the surface of the heart and the target would be invisible. Also, the retained blood would be caked to become a clot D. Therefore, such a clot has to be removed during the surgery.

Specifically, holding forceps 5 are inserted in the view field of the pericardial cavity C, through the sheath 2 which has the rigid scope 1 inserted therein, or through another sheath 2 which is inserted from a different route. Thereafter, the clot D is held by the holding forceps 5 and taken out from the sheath 2. At this time, if the clot D is large, the holding forceps 5 are rotated while holding the clot D to entwine the clot D on the distal end of the holding forceps 5. Then, the holding forceps 5 and the clot D are taken out through the sheath 2. By so doing, the clot D can be effectively removed in a state where the rigid scope 1 is inserted in the pericardial cavity C.

The catcher unit of the distal end of the holding forceps 5 may be made of a rubber or such a material, and the material and the structure may be capable of readily catching and holding the clot D. The mouth of the distal end of the sheath 2 may have a largely openable structure, or may be provided with a basket-shaped receiver so as to avoid such a situation that the clot D is entangled by the exit of the sheath 2 and drops off into the pericardial cavity C.

In addition, a suction catheter, a DC (Direct Coronary atherectomy) device which is retractable in the distal end, basket forceps, a pouch, or such a device for use in the digestive tract may also be adopted instead of the holding forceps 5.

The above-mentioned rigid scope 1 may be, specifically, a rigid scope of a relay lens system, being a type of a scope which transmits an image signal to the hand side by a camera head or such an imaging element. Alternatively, it may also be a type of a scope which has an imaging element on the distal end and one or more connectors through which cable(s) from the imaging element can be connected to a processor, or may be a type of a scope which can directly transmit a signal of an imaging element to the outside the body in a wireless manner. The wireless transmitter may be arranged on either the distal end or on the hand side. Moreover, the distal end portion of the rigid scope 1 may also have a bending mechanism made from a wire or the like for bending. Regarding the bending direction, it is either possible to adopt two directions, meaning up and down, or four directions, meaning left, right, up, and down. By using the bending mechanism, only the view field direction can be changed without changing the insertion angle, in a state where the heart and the pericardium are being lifted up by the shaft of the rigid scope inserted in the pericardial cavity. This makes it possible to conduct the operation in much easier and simpler manner. The imaging element may use CCD, CMOS, or the like. The illumination means may use LED or a light guide. Alternatively, illumination light may also be irradiated from a different source. In addition, the rigid scope 1 may also have one or more channels for inserting surgical instruments, or a lens cleaning function. The view field direction may be any of the straight view, the lateral view, or the oblique view (30, 45, or 70 degrees).

The insertion part of the rigid scope 1 may be formed with a hollow like a rigid pipe to have a structure through which only the imaging element can be withdrawn or inserted again. By so doing, only the observation unit can be made detachable.

In addition, the bed for the patient may be configured such that the contour can be changed at its option. For example, the most observable shape of the pericardial cavity C can be created by arching only the chest region forward or backward. The optimum repositioning of the body posture may also be calculated from the anatomical information that has been obtained in advance from CT, MRI, or the like.

In the abovementioned embodiments, the description has been made regarding the posture repositioning step (S4A) for securing the space on the left ventricle side as shown in FIG. 5, and the posture repositioning step (S4B) for securing the space on the right ventricle side as shown in FIG. 8. However, the body posture may also be repositioned in the right lateral recumbent position for observing the posterior side of the heart, the lateral side of the left ventricle, the posterior side wall of the left ventricle, or the left pulmonary veins L. Moreover, the body posture may also be repositioned in the left lateral recumbent position for observing the posterior side of the heart, the lateral side of the right ventricle, the lateral side/posterior side wall of the right atrium, the superior/inferior vena cava sides, or the right pulmonary veins R.

In addition, in the abovementioned embodiments, the description has been made regarding the case where the posture repositioning step (S4A) is performed after performing the step to the guide rigid scope 1 to the lateral wall of the left ventricle (S5A) as shown in FIG. 6. However, this should not be construed as limiting. The posture repositioning step may also be performed before or after opening a hole by penetrating the pericardium P with a puncture needle, before or after inserting the sheath 2, before or after inserting the rigid scope 1, before or after inserting the ablation device 3, or before or after observing or treating the surgical site.

The present invention offers an effect of enabling to observe the affected part in an easy and simple manner by using the insertion part of the rigid endoscope itself to actively move the surrounding organs around the affected part so that thereby the affected part can be reached by the rigid endoscope.

What is claimed is:

1. An operation method of a rigid endoscope, the method comprising:
   a sheath insertion step of percutaneously inserting at least one flexible sheath in a pericardial cavity of a heart;
   an insertion step of inserting a rigid scope in the flexible sheath;
   a view field securing step for securing the view field for a surgical site within the pericardial cavity;
   a guide step for guiding the rigid scope to the surgical site; and
   an observation step of observing the surgical site with the rigid scope.

2. An operation method of a rigid endoscope according to claim 1, wherein the view field securing step is a step of securing the view field by lifting up the pericardium with a shaft part of the rigid scope through operation of a hand-side unit of the rigid scope with a vicinity of a subxiphoid acting as a fulcrum, in a state where the rigid scope is inserted from the subxiphoid into the pericardial cavity.

3. An operation method of a rigid endoscope according to claim 1, wherein the view field securing step includes a posture repositioning step of repositioning the posture of a patient so that a distal end of the rigid scope can be disposed on an upper side of the heart within the pericardial cavity.

4. An operation method of a rigid endoscope according to claim 1, wherein the view field securing step includes a space securing step of expanding an open space of the pericardial cavity by looping a guide wire around the heart within the pericardial cavity to thereby pull the pericardium apart from the heart by utilizing the elasticity of the guide wire.

5. An operation method of a rigid endoscope according to claim 1, wherein the view field securing step is a step of securing the view field by moving an organ inside the view field of the surgical site with use of the guide wire which is inserted in the pericardial cavity.

6. An operation method of a rigid endoscope according to claim 1, wherein the view field securing step includes
   a first step of inserting a distal end of the rigid scope into a posterior side of the heart and inserting the distal end of the rigid scope into a space between the heart and the pericardium, and
   a second step of lifting up the heart up with use of a shaft part of the rigid scope that has been disposed on a tangential direction of the heart; and
   the guide step is a step of repeating the first step and the second step to thereby make the distal end of the rigid scope closer to a base side on the posterior side of the heart.

7. An operation method of a rigid endoscope according to claim 1, wherein the view field securing step is a step of securing the view field by expanding an open space of the pericardial cavity by pulling an inflatable unit that is provided on a distal end of the rigid scope, in a direction outward from the body, to thereby pull the pericardium apart from the heart.

8. An operation method of a rigid endoscope according to claim 1, wherein the view field securing step is a step of securing the view field by expanding an open space of the pericardial cavity by pulling an inflatable unit that is provided on a distal end of the flexible sheath, in a direction outward from the body, to thereby pull the pericardium apart from the heart.

9. An operation method of a rigid endoscope according to claim 1, wherein the view field securing step is a step of securing the view field by expanding an open space of the pericardial cavity by pulling an inflatable unit that is a separate unit from the rigid scope but is inserted with the rigid scope in the pericardial cavity through the flexible sheath, in a direction outward from the body, to thereby pull the pericardium apart from the heart.

10. An operation method of a rigid endoscope according to claim 1, wherein the view field securing step includes a clot removal step of removing a clot that covers to obscure the surface of the heart within the pericardial cavity, with a clot removal unit.

11. An operation method of a rigid endoscope according to claim 10, wherein the clot removal step includes:
    a step of catching and holding the clot by inserting a catcher unit that has been inserted from the flexible sheath, to the pericardial cavity;
    a step of wrapping the clot around the catcher unit by rotating the catcher unit; and
    a step of taking out the clot together with the catcher unit to the outside of the body through the flexible sheath.

12. An operation method of a rigid endoscope according to claim 1, wherein the guide step is a step of guiding a distal end of the rigid scope to a posterior side of the heart in a state where the rigid scope is inserted from the subxiphoid into the pericardial cavity.

13. An operation method of a rigid endoscope according to claim 12, wherein the guide step includes a rotation step of operating a shaft part of the rigid scope with a vicinity of the subxiphoid acting as a fulcrum while pushing the distal end of the endoscope onto the pericardium side, to thereby guide the rigid scope to the posterior side of the heart along the pericardial cavity.

14. An operation method of a rigid endoscope according to claim 13, wherein the rotation step is a step of guiding the distal end of the rigid scope from the lateral wall of the left ventricle to the posterior side of the heart while rotating the shaft part of the rigid scope clockwise.

15. An operation method of a rigid endoscope according to claim 13, wherein the rotation step is a step of guiding the distal end of the rigid scope from the lateral wall of the right ventricle to the posterior side of the heart while rotating the shaft part of the rigid scope anticlockwise.

16. An operation method of a rigid endoscope according to claim 1, wherein the guide step is a step of guiding a flexible distal end portion of the flexible sheath and a distal end of the rigid scope to a posterior side of the heart in a state where the flexible distal end portion is inserted from the subxiphoid into the pericardial cavity of the anterior wall of the heart.

17. An operation method of a rigid endoscope according to claim 16, wherein the guide step includes
a step of inserting the distal end of the rigid scope into a middle of the inside of the flexible sheath,
a step of pushing the rigid scope and the flexible sheath onto the abdomen so that thereby the insertion route from the subxiphoid to the pericardium can move to the dorsal side, and
a step of operating a shaft of the rigid scope so that thereby the flexible distal end portion of the flexible sheath that has been inserted in the pericardial cavity can pass by the lateral wall of the heart and move to the posterior side of the heart.

18. An operation method of a rigid endoscope according to claim 1, wherein the guide step is a step of guiding a distal end of the rigid scope to the posterior wall of the heart in a state where the distal end of the rigid scope is inserted from the subxiphoid into the pericardial cavity in front of the anterior wall of the heart, through the flexible sheath.

19. An operation method of a rigid endoscope according to claim 18, wherein the guide step includes
a step of pushing the rigid scope and the flexible sheath onto the abdomen,
a lateral wall moving step of moving the distal end of the rigid scope parallelly from the anterior wall to the lateral wall of the heart along the surface of the heart, and
a posterior wall moving step of moving the distal end of the rigid scope parallelly from the lateral wall to the posterior wall of the heart along the surface of the heart.

20. An operation method of a rigid endoscope according to claim 1, wherein the observation step is a step of conducting the observation only by exchanging a detachable observation unit of the rigid scope.

21. An operation method of a rigid endoscope according to claim 1, wherein the observation step is a step of conducting the observation by bending a distal end portion of the rigid scope.

22. An operation method of a rigid endoscope according to claim 21, wherein the distal end portion of the rigid scope has a bending mechanism for bending.

23. An operation method of a rigid endoscope according to claim 7, wherein the inflatable unit on the distal end of the rigid scope is a balloon.

* * * * *